(12) United States Patent
Stroock et al.

(10) Patent No.: US 9,766,173 B2
(45) Date of Patent: Sep. 19, 2017

(54) MULTIMODAL SENSOR INCLUDING A TENSIOMETER, METHOD OF USE AND FABRICATION

(71) Applicant: Cornell University, Ithaca, NY (US)

(72) Inventors: Abraham D. Stroock, Ithaca, NY (US); Alan N. Lakso, Geneva, NY (US); Vinay Pagay, Ithaca, NY (US); Michael Santiago, Naguabo, PR (US); David Sessoms, St. Paul, MN (US)

(73) Assignee: Cornell University, Ithaca, NY (US)

(*) Notice: Subject to any disclaimer, the term of this patent is extended or adjusted under 35 U.S.C. 154(b) by 98 days.

(21) Appl. No.: 14/898,003

(22) PCT Filed: Jun. 14, 2014

(86) PCT No.: PCT/US2014/042435
§ 371 (c)(1),
(2) Date: Dec. 11, 2015

(87) PCT Pub. No.: WO2014/201442
PCT Pub. Date: Dec. 18, 2014

(65) Prior Publication Data
US 2016/0139021 A1    May 19, 2016

Related U.S. Application Data

(60) Provisional application No. 61/835,224, filed on Jun. 14, 2013.

(51) Int. Cl.
*G01N 7/10* (2006.01)
*G01N 13/02* (2006.01)
*G01N 33/24* (2006.01)

(52) U.S. Cl.
CPC .............. *G01N 13/02* (2013.01); *G01N 7/10* (2013.01); *G01N 33/246* (2013.01)

(58) Field of Classification Search
CPC ........ G01N 7/10; G01L 9/0045; G01L 33/246
See application file for complete search history.

(56) References Cited

U.S. PATENT DOCUMENTS 4,475,749 A    10/1984  Pforr et al.
5,224,769 A *   7/1993  Holbrook .............. G01N 27/223
                                                     324/664

(Continued)

OTHER PUBLICATIONS

International Search Report and Written Opinion of the ISA for corresponding International Application No. PCT/US14/42435, date of mailing Oct. 21, 2014 (10 pgs).

(Continued)

*Primary Examiner* — Justin Olamit
(74) *Attorney, Agent, or Firm* — Harris Beach PLLC

(57) ABSTRACT

A multimodal sensor includes a microtensiometer for measuring the chemical potential of a sub-saturated liquid, a temperature sensor, and a water content sensor. The microtensiometer includes a sensor body comprising a first gas-impermeable layer, an opposing second gas-impermeable layer, and a porous membrane layer disposed therebetween. The sensor body defines an internal liquid reservoir. The membrane layer is fluidly connected with the liquid reservoir, and extends to an outside edge of the microtensiometer. The membrane layer defines a plurality of through pores providing an open path from the liquid reservoir to the outside edge of the microtensiometer. The pores have a maximum diameter of 3 millimeters. The microtensiometer further includes a sensor adapted to measure changes in pressure between the liquid reservoir and an outside environment. The temperature sensor is integrated onto the microtensiometer body, and the water content sensor is coupled to the microtensiometer body.

23 Claims, 12 Drawing Sheets

(56) References Cited

U.S. PATENT DOCUMENTS

| | | | |
|---|---|---|---|
| 5,872,447 A | 2/1999 | Hager, III | |
| 6,752,007 B1* | 6/2004 | Hubbell | E02D 1/027 |
| | | | 73/73 |
| 8,695,407 B2* | 4/2014 | Stroock | G01N 13/02 |
| | | | 137/78.3 |
| 2011/0146956 A1 | 6/2011 | Stroock et al. | |
| 2011/0290304 A1 | 12/2011 | Daniel | |
| 2012/0079876 A1 | 4/2012 | Stroock et al. | |

OTHER PUBLICATIONS

Stroock, A., et al. Plant-Mimetic Heat Pipes for Operation With Large Inertial and Gravitational Stresses, Report, Aug. 16, 2012, pp. 1-16.

* cited by examiner

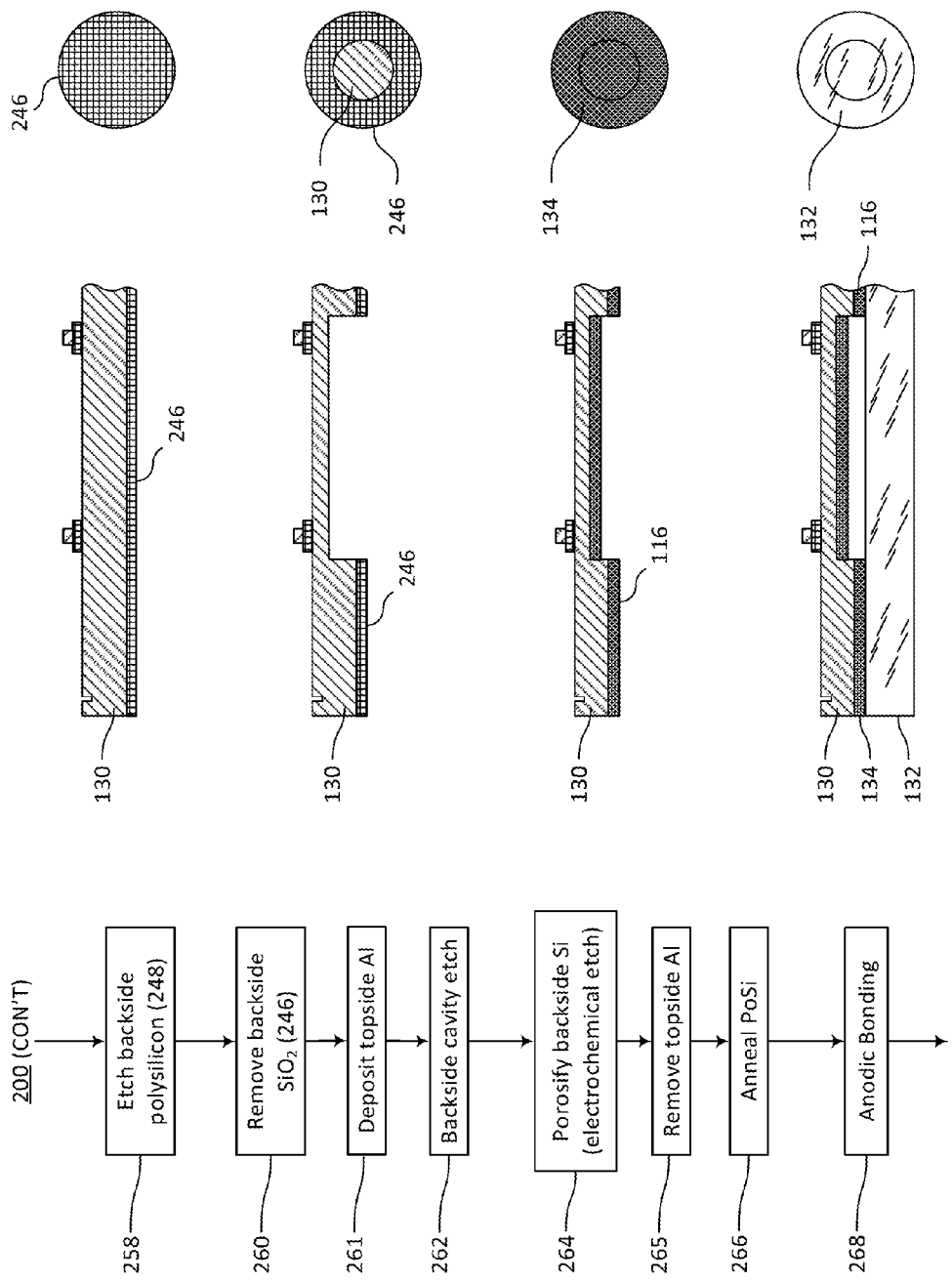
FIG. 9 (CON'T)

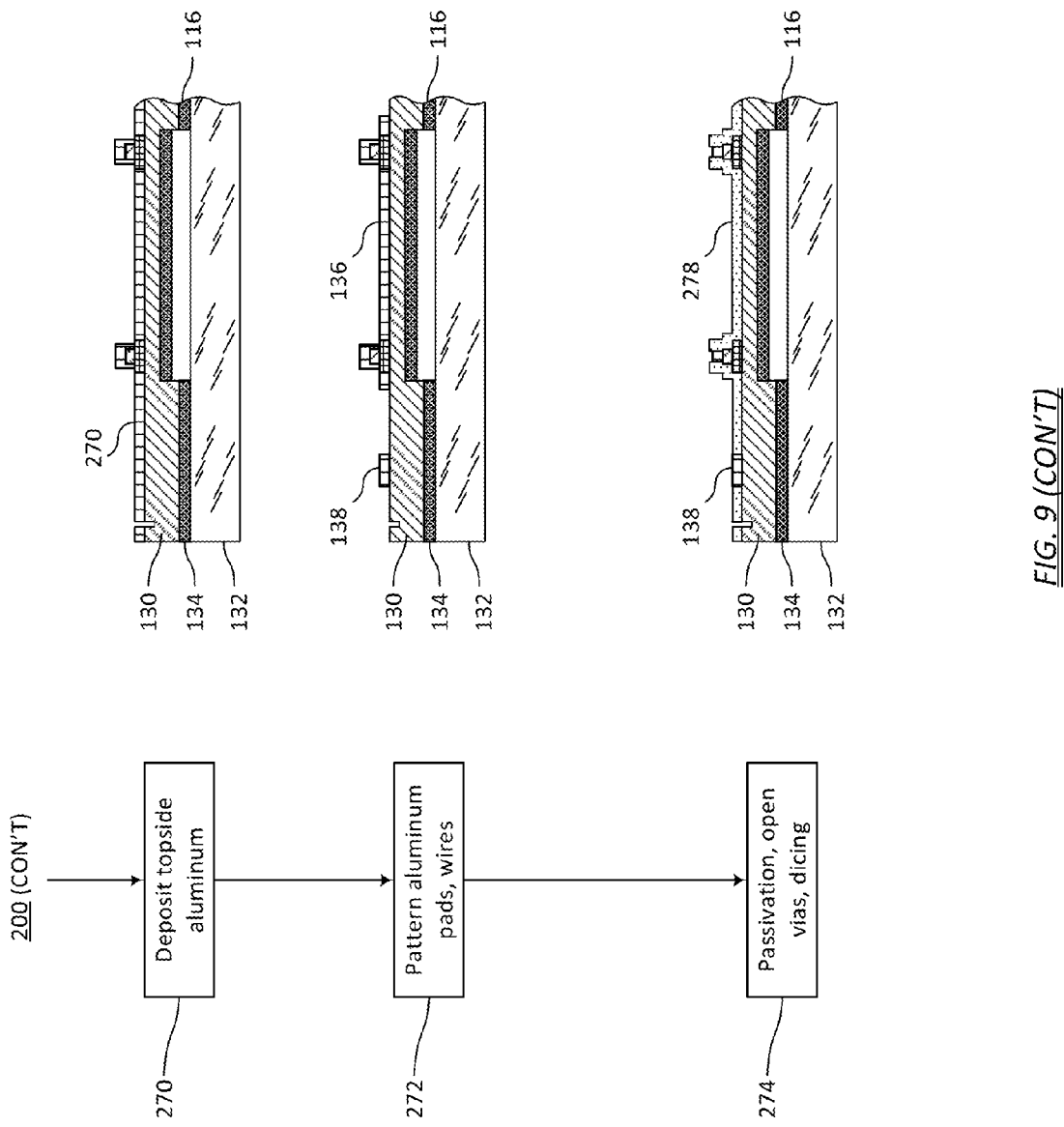

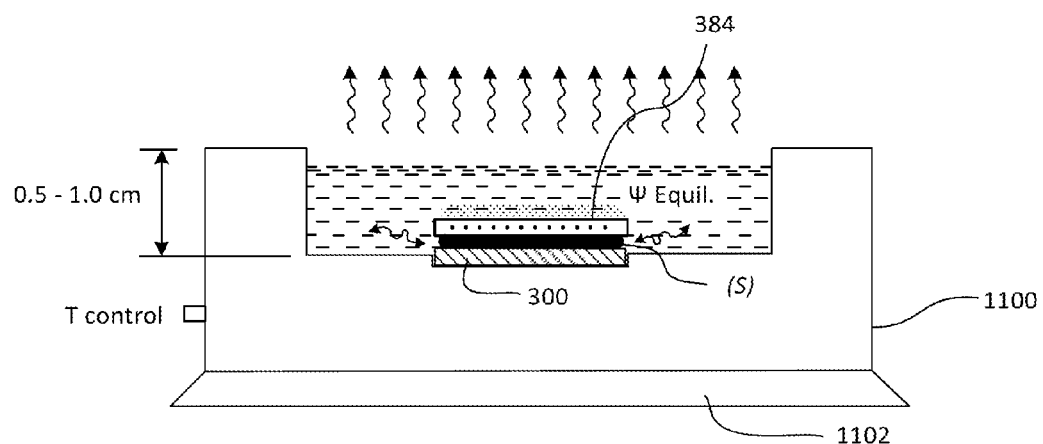
*FIG. 15*
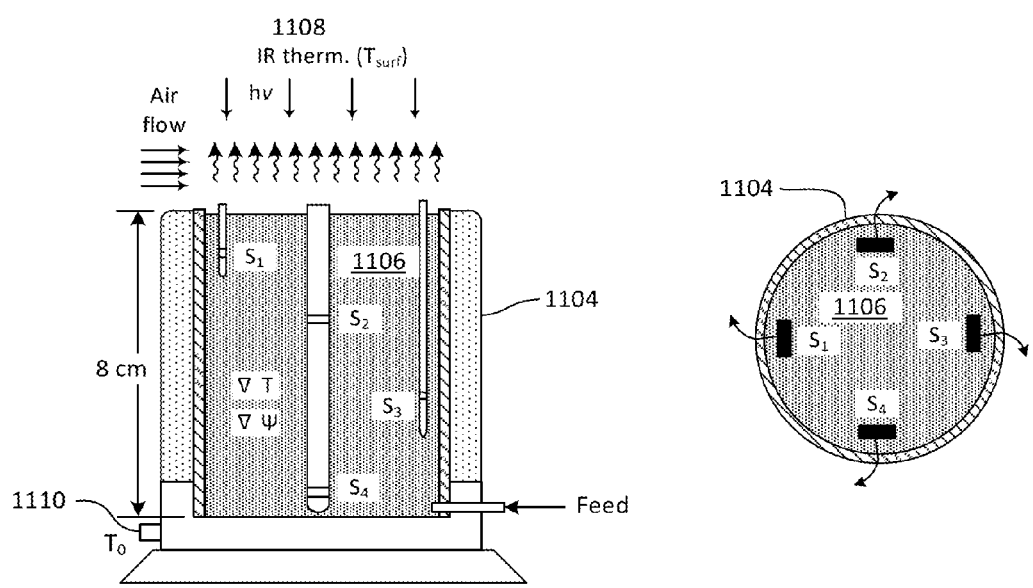
*FIG. 16*  *FIG. 17*

MULTIMODAL SENSOR INCLUDING A TENSIOMETER, METHOD OF USE AND FABRICATION

CROSS REFERENCE TO RELATED APPLICATION

This application is a national stage (371) application of PCT/US2014/042435 filed Jun. 14, 2014, entitled MULTIMODAL SENSOR, METHOD OF USE AND FABRICATION, which claims priority to and the benefit of U.S. Provisional Application Ser. No. 61/835,224, filed Jun. 14, 2013, entitled "MICROTENSIOMETER SENSOR, PROBE AND METHOD OF USE", which applications are incorporated herein in their entirety by reference.

FIELD OF THE INVENTION

This disclosure relates generally to microelectromechanical sensors and, more specifically, to a microtensiometer for measuring chemical potential at negative pressures or in sub-saturated phases.

BACKGROUND OF THE INVENTION

In both natural and technological contexts, the degree of saturation with respect to water often plays a central role in defining a system's properties and function. For example, in the atmosphere, relative humidity is a critical meteorological indicator, and is important to evaporative demand on soil, bodies of water, and the biosphere. In the context of plants and agriculture, water saturation in the soil and atmosphere controls viability, growth potential, yield, and quality of crop. In foods, water activity affects taste, texture, and stability with respect to bacterial and fungal growth. In chemical and biological processes, the osmotic strength of aqueous solutions controls the kinetics and thermodynamics of reactions and the stability of cells, proteins, and materials. Additionally, the water status and dynamics of water in concrete is critical to final quality.

The chemical potential of water, $\mu_w$ [J mol$^{-1}$], within a phase or host material provides the most generally useful measure of the degree of hydration. This thermodynamic state variable quantifies the free energy of water molecules and thus their accessibility for chemical reactions and physical exchange with other phases or materials. For example, regardless of the local mode of transport, the driving force for mass transfer can be expressed as a gradient of chemical potential. The chemical potential of water can be characterized with two convenient state variables. The first is activity, $a_w$, defined as the relative humidity of a vapor in equilibrium with the phase of interest ($a_w = p/p_{sat}(T)$, where p and $p_{sat}(T)$ are the vapor pressure and saturation vapor pressure at temperature T, respectively). The second is water potential, $\Psi_w$ [MPa], the deviation of the chemical potential from its value at saturation divided by the molar volume of liquid water ($\Psi_w = \mu_w - \mu_0(T))/v_{w,liq}$). Water potential is widely used in the plant and soil science communities. The typical water potential range of plants and soils is $-0.001 > \Psi_w > -3.0$ MPa ($0.99999 > a_w > 0.978$).

For in situ measurements, existing methods of hygrometry include capacitance, resistance, thermal conductivity, psychrometric, and tensiometric. Capacitance, resistance, and dielectric methods measure the corresponding electronic property of a calibrated material within the sensor that is allowed to reach its equilibrium hydration with the phase of interest. Although these methods allow for small form factors (e.g., <1 cm$^2$ sensing areas), they suffer drawbacks. One drawback is that they generally provide moderate-to-low accuracy for drier conditions (i.e., ±~0.02 in activity for $a_w < 0.9$; ±~3 MPa in water potential). Another drawback is they become less accurate above this range (i.e., ±25% of measurement of water potential for the MPS-2 dielectric hygrometer by Decagon), and the response time 10-60 minutes. Despite their limited accuracy, resistive and capacitive sensors are widely used for coarse measurements of water status in soils for irrigation scheduling.

Psychrometry, and thermocouple psychrometry in particular, has been heavily studied for in situ hygrometry in the environmental context. Thermocouple psychrometry involves the measurement of the dew point temperature on a wetted thermocouple evaporating into a volume of air that separates it from the sample of interest. It is a transient, non-equilibrium process. The range of commercial psychrometers is reported by the manufacturer to be 0.999 to 0.93 in activity and $-0.1$ to $-10$ MPa in water potential with an accuracy of ±0.001 in activity and ±0.1 MPa in water potential. These devices have good response time (~1 min.), however, they are temperature-sensitive and expertise is required for installation.

Tensiometers operate on the principle of equilibration between a sample of interest and an internal volume of liquid water via a vapor gap and a porous membrane. Commercially-available tensiometers consist of an air-tight, water-filled tube with a porous ceramic tip at the bottom and a vacuum gauge at the top. The tensiometer is partly buried in the soil to a suitable depth, and the ceramic tip allows water to move freely in or out of the tube. As the soil dries out, water is sucked out through the porous ceramic tip, reducing the pressure inside the tensiometer to values below atmospheric pressure; this pressure is read on the vacuum gauge. When the soil is wetted by sufficient rainfall or irrigation, water flows back into the tensiometer, the pressure rises and the gauge reading rises.

Commercially-available tensiometers have a small range of 1 to 0.9988 in activity or 0 to $-0.16$ MPa in water potential with an excellent accuracy of ±5×10$^{-4}$ MPa in water potential. However, they have a long response time (~30 min.) and they fail due to invasion of air or cavitation beyond this range. Despite the extremely limited range and large form factors of conventional tensiometers (sensing area>10 cm$^2$), their unmatched accuracy near saturation means that they are used extensively to monitor the water potential in soils for irrigation scheduling for amoral crops that require moist conditions to grow.

Current research efforts have pursued two strategies to extend the operational range of tensiometers. The first strategy used porous membranes with smaller pore sizes to achieve stability out to $\Psi_w = -1.5$ MPa ($a_w \cong 0.99$). However, these so-called "high capacitance tensiometers" have similar form factors as those of conventional tensiometers. The second strategy used osmotic solutions within the internal volume of the tensiometers to extend the stability limit. This approach has been refined and demonstrated out to $\Psi_w = -1.6$ MPa ($a_w = 0.988$) with a reduced form factor (1.5 cm$^2$).

Furthermore, local water content and chemical potential define the physical properties of materials, the rates of chemical transformations, and the accessibility of water for exchange within the local environment. Fluxes of water are strongly coupled to and, in many cases, control the transport of energy and other chemical species. The ability to understand and predict natural processes such as climate change and optimize human processes such as irrigation depend on the ability to measure water content, chemical potential, and flux quantitatively, with appropriate spatial and temporal resolution and accounting for their complex coupling to temperature, material properties, and biological response.

SUMMARY OF THE INVENTION

The inventors have noted that the tensiometric approach presents a promising route to accurate measurements of chemical potential across the range near saturation ($a_w > 0.93$, $\Psi_w > -10$ MPa) if the stability limit can be significantly extended. Disclosed herein is a microelectromechanical system (MEMS) that spans the entire water potential range of plants and soils (e.g., $-0.001 > \Psi_w > -3.0$ MPa; $0.99999 > a_w > 0.978$) with a form factor that is compatible with in situ measurements within complex environments such as soils and plant tissues. The smaller sensor allows for measurements with higher spatial resolution and for embedding of the sensor within complex samples such as the vascular tissues of living plants. The MEMS approach helps extend the stability limit by minimizing the internal volume of the liquid that is placed at reduced pressure, minimizing the presence of impurities, which often lower the energetic barrier to nucleation, and allowing for the formation of the exchange membrane in well-defined, nanoporous materials such as porous silicon.

In accordance with one aspect of the disclosure, a microtensiometer includes a sensor body comprising a first gas-impermeable layer and an opposing second gas-impermeable layer. The sensor body defines a sealed internal liquid reservoir. The microtensiometer further includes a porous membrane layer disposed between the first and second gas-impermeable layers. The membrane layer is in fluid contact with the liquid reservoir, and extends to an outside edge of the microtensiometer. The membrane layer defines a plurality of through pores. The pores provide an open path from the liquid reservoir to the outside edge of the microtensiometer. The pores have a maximum diameter of 3 millimeters. The microtensiometer further includes a sensor adapted to measure changes in pressure between the liquid reservoir and an outside environment.

In another aspect of the disclosure, a multimodal sensor includes a microtensiometer adapted to measure the chemical potential of a sub-saturated liquid, a temperature sensor, and a water content sensor. The microtensiometer includes a sensor body comprising a first gas-impermeable layer and an opposing second gas-impermeable layer. The sensor body defines a sealed internal liquid reservoir. The microtensiometer further includes a porous membrane layer disposed between the first and second gas-impermeable layers. The membrane layer is in fluid contact with the liquid reservoir, and extends to an outside edge of the microtensiometer. The membrane layer defines a plurality of through pores. The pores provide an open path from the liquid reservoir to the outside edge of the microtensiometer. The pores have a maximum diameter of 3 millimeters. The microtensiometer further includes a sensor adapted to measure changes in pressure of the liquid reservoir. The temperature sensor is integrated onto the microtensiometer body, and the water content sensor is coupled to the microtensiometer body.

BRIEF DESCRIPTION OF THE DRAWINGS

The features described herein can be better understood with reference to the drawings described below. The drawings are not necessarily to scale, emphasis instead generally being placed upon illustrating the principles of the invention. In the drawings, like numerals are used to indicate like parts throughout the various views.

FIG. 15 depicts a cross sectional view of an apparatus for calibrating the thin film wave guide shown in FIG. 12;

FIG. 16 depicts a cross sectional view of an apparatus for characterizing a soil sample;

FIG. 17 depicts is a top view of the apparatus shown in FIG. 16;

DETAILED DESCRIPTION OF THE INVENTION

Figure 1:
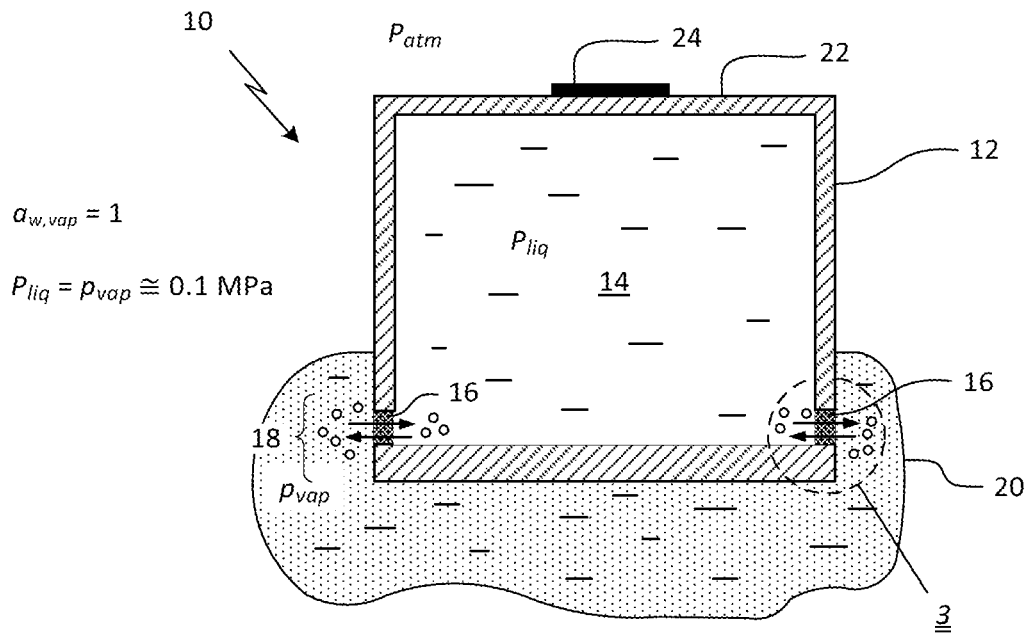
FIG. 1 depicts a cross sectional view of a tensiometer in equilibrium with a subsaturated environment according to one embodiment of the present invention.

The concept of tensiometry is based on the coupling of liquid water to vapor via a wettable porous membrane. Referring to FIG. 1, a tensiometer 10 according to one embodiment of the invention includes a body 12 enclosing a liquid reservoir 14. A porous membrane 16 is fluidly coupled on one side to the liquid reservoir 14, and on the other side to an external phase of interest, or vapor interface 18, of a sample 20. In the illustrated embodiment, the body 12 is formed of silicon and serves as a backbone structure for the microtensiometer elements, the liquid reservoir 14 contains a sealed volume of water, and the tensiometer 10 is shown inserted into a soil sample 20. The tensiometer 10 includes a flexible diaphragm 22 and a sensor 24 attached or integral thereto. In one embodiment, the sensor 24 is a strain gauge. Changes in hydrostatic pressure within the liquid reservoir 14 can be determined by measuring the deflection of the diaphragm 22 via the strain gauge 24. In FIG. 1, the bulk liquid 14 is in equilibrium with the saturated vapor 18 of the soil sample 20 ($P_{liq}=P_{atm}\cong 0.1$ MPa). That is, liquid-vapor equilibrium exists and no net evaporation occurs from the bulk liquid reservoir 14.

Chemical equilibration occurs between a macroscopic volume of pure liquid inside the reservoir 14 and a vapor that itself is in equilibrium with the chemical potential of the phase of interest 20 outside the device 10. As used herein, a macroscopic volume is a large enough volume-to-surface area ratio to minimize wall interactions that could affect the thermodynamic properties of the liquid (e.g., the smallest cavity dimension is greater than ~1 μm). Equation (1) expresses chemical equilibration as:

$$\mu_{w,liq}(T,P_{liq}) = \mu_{w,vap}(T,p_{vap}) = \mu_{sample} \quad (1)$$

Figure 2:
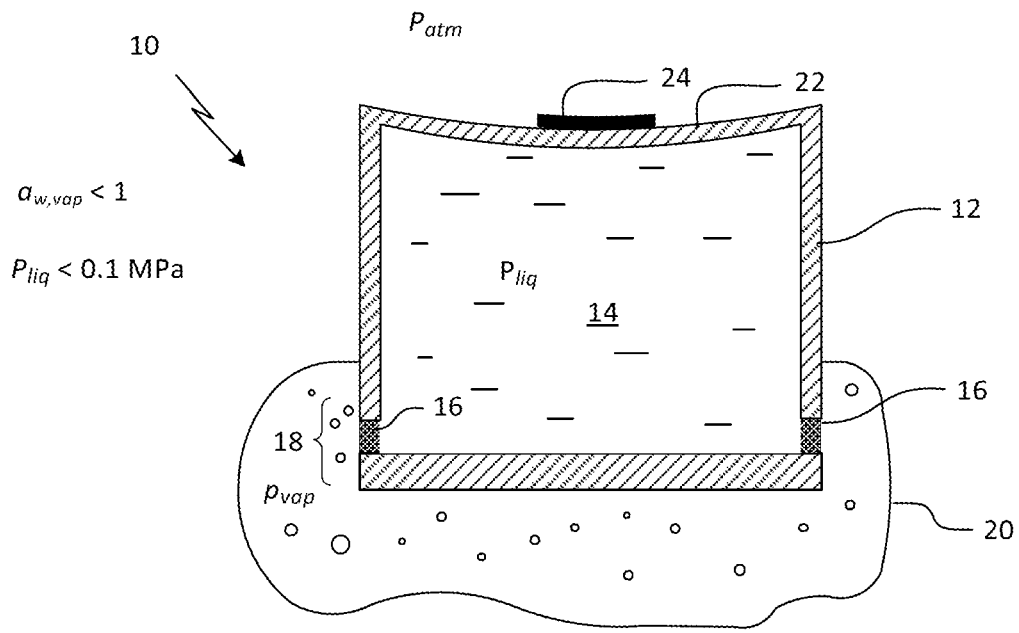
FIG. 2 depicts a cross sectional view of the tensiometer of FIG. 1 in subsaturated conditions.
Figure 3:
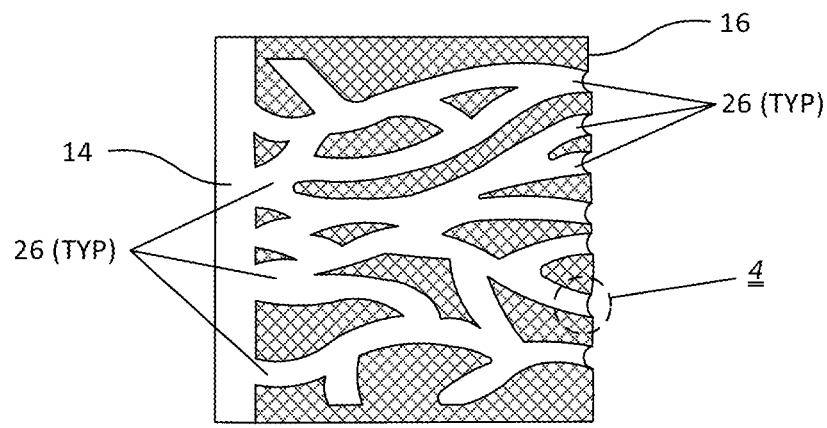
FIG. 3 depicts an enlarged view of the porous membrane shown in FIG. 1.
Figure 4:
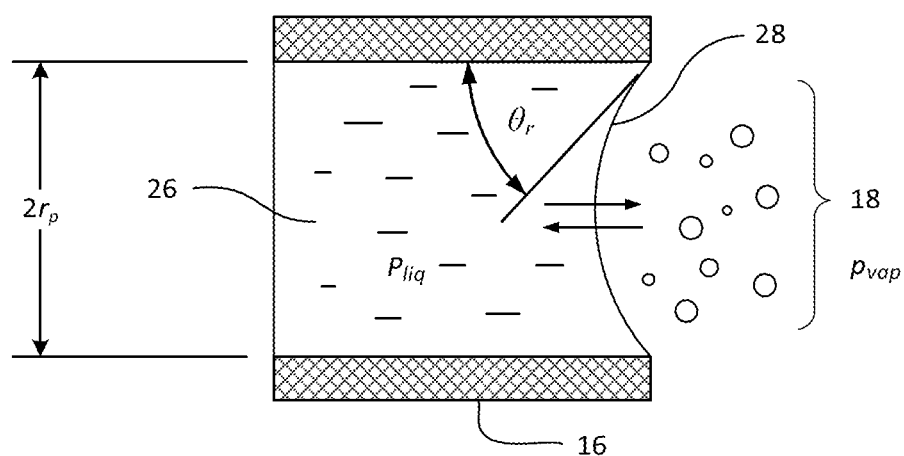
FIG. 4 depicts an enlarged view of a pore shown in FIG. 3.

Referring to FIGS. 2-4, when exposed to a sub-saturated external phase, the pure water in the tensiometer 10 will evaporate from the external surface of the membrane 16. This loss of fluid will reduce the pressure in the bulk phase ($P_{liq}$) within the cavity 14. This reduction of pressure will lower the chemical potential ($\mu_{liq}$) of the internal liquid. If the liquid phase remains intact, i.e., does not change phase to vapor (cavitate), the pressure will decrease until the internal and external chemical potentials are equal and transfer of water will cease. The pressure at which this equilibrium will occur can be found by expanding the expressions for the chemical potential of the pure liquid and vapor (ideal gas) in equation (1):

$$\mu_0(T) + \int_{P_{atm}}^{P_{liq}} v_{w,liq}(P'_{liq},T)dP'_{liq} = \mu_0(T) + RT\ln(a_{w,vap}) = \mu_{sample} \quad (2)$$

where $\mu_0(T)$ [J mol$^{-1}$] is the chemical potential of water on the vapor-liquid coexistence line (in the presence of $P_{atm}$, of air) at temperature T [K], $v_{w,liq}$ [m$^3$ mol$^{-1}$] is the molar volume of the liquid, R=8.314 [J mol$^{-1}$ K$^{-1}$] is the ideal gas constant, and $a_{w,vap}=p_{vap}/p_{sat}(T)$=relative humidity (%)/100 is the activity of the vapor at temperature, T. In equation (2), the liquid is assumed to be pure ($a_{w,liq}=1$). If one also assumes that the internal liquid is inextensible ($v_{w,liq}$=constant), equation (2) can be solved for the pressure of water inside the tensiometer cavity, $P_{liq}$, at equilibrium:

$$P_{liq} = P_{atm} + \frac{RT}{v_{w,liq}}\ln(a_{w,vap}) = P_{atm} + \frac{\mu_{sample}-\mu_0}{\mu_{w,liq}} = P_{atm} + \Psi_w \quad (3)$$

Equation (3) can be rearranged to provide relationships between the water potential of a phase of interest ($\Psi_w$), the pressure difference between the internal liquid and the atmosphere, and the activity of the vapor that mediates their equilibrium:

$$\Psi_w = P_{liq} - P_{atm} = \frac{RT}{v_{w,liq}}\ln(a_{w,vap}) \quad (4)$$

The relations in equation (4) hold within the approximation of constant molar volume of the liquid. Equation (4) demonstrates that the water potential is the pressure difference across the tensiometer 10. In other words, a tensiometer provides a direct, approximate measurement of water potential.

Equation (4) also illustrates the unusual sensitivity of tensiometry near saturation: for $a_w=1+\Delta a_w$ with $\Delta a_w \ll 1$, the water potential at room temperature (T=293 K) can be expressed as:

$$\Psi_w \cong \frac{RT}{v_{w,liq}}\Delta a_w \cong 135\Delta a_w \quad [MPa] \quad (5)$$

For example, for a 1% reduction in activity from saturation ($\Delta a_w=-0.01$), the diaphragm 22 of the tensiometer experiences a difference of pressure (from equation (5)) of $\Psi_w = P_{w,liq} - P_{atm} \cong -1.3$ MPa. The microtensiometer disclosed herein is projected to measure pressure differences as small as $10^{-6}$ MPa with appropriate design of the diaphragm 22 and sensor 24, allowing for extreme sensitivity to small changes in saturation.

FIG. 3 depicts a portion of the membrane 16 at the interface of the liquid reservoir 14. The pores 26 couple the external vapor 18 with bulk water inside the reservoir. FIG. 4 depicts an enlarged view of a single pore 26 within the porous membrane 16 showing a concave air-liquid interface 28. In FIG. 4, $r_p$ indicates the pore radius and $\theta_r$ indicates the contact angle of the liquid with the wall of the membrane. Equation (3) states that the pressure in the bulk, internal liquid, $P_{liq}$ will decrease as the activity or water potential in the external environment decreases. As this pressure drops below ambient, $P_{atm}\cong 0.1$ MPa, it becomes susceptible to the invasion of air through the pores 26 of the membrane 16 and to cavitation (formation of gas bubbles). Invasion of air will occur through the pores of the membrane when:

$$P_{liq} - P_{atm} < \frac{2\sigma\cos\theta_r}{r_{p,max}} \quad (6)$$

where σ is the surface tension of water [0.072 N m$^{-1}$], $\theta_r$ [rad] is the receding contact angle of the liquid with the pore wall, $r_{p,max}$[m] is the radius of the largest pore that spans the membrane. The threshold in equation (6) represents the Young-Laplace pressure across a curved meniscus; for nanoscopic pores, it can only serve as a rough estimate of the threshold. For $p_{sat}<P_{liq}<P_{atm}$, the internal liquid will be supersaturated with respect to air unless it has been degassed, and, therefore, be prone to cavitation by formation of bubbles of air. For lower pressures, $P_{liq}<p_{sat}$, the liquid will also be superheated and prone to cavitation via the formation of bubbles of vapor (boiling). In the absence of pre-existing pockets of gas within the cavity, these two modes of cavitation will be kinetically limited and the liquid will be metastable. In conventional tensiometers, with macroscopic internal volumes and membranes with micrometer-scale pores, the stability limit tends to be $|P_{liq}-P_{atm}|<0.1$ MPa, or $a_{w,vap}>0.999$. The microtensiometer disclosed herein significantly extends this limit. In one example, the use of nanoporous membranes and smaller internal volumes permits $|P_{liq}-P_{atm}|>20$ MPa and $a_{w,vap}<0.86$.

Equations (4) and (6) can provide an important link between the desired range of operation and the required size of pores in the membrane. For example, the equations can be rewritten as:

$$\Psi_w = P_{liq} - P_{atm} > -\frac{2\gamma\cos\theta_r}{r_{p,max}} \quad (7)$$

Assuming the minimum relevant range of Ψ is $0 > \Psi > -5 \times 10^{-5}$ MPa, based on Equation (7) above, the largest pores in the membrane for this range must be smaller than ~3 mm. In a practical sense, to add a margin of safety, a largest pore diameter of 0.3 mm would be adequate. In another example, a range of $0 > \Psi > -10^2$ MPa would be desirable. For this condition, one would need pores of radius less than one nanometer.

Figure 5:
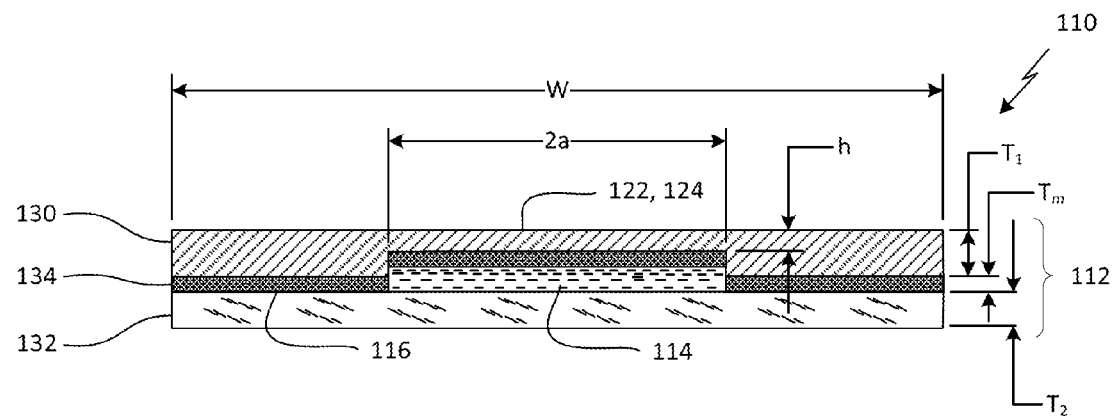
FIG. 5 depicts a cross sectional view of a microtensiometer according to one embodiment of the present invention.

Turning now to FIG. 5, wherein like numerals indicate like elements in FIGS. 1-4, a cross sectional view of a microtensiometer 110 is shown according to one embodiment of the present invention. The microtensiometer 110 is a microfluidic sensor based on microelectromechanical system (MEMS) technology for the purpose of measuring the chemical potential of water in woody plants, soils, and other systems where sub-saturated liquids or vapors exist. In one embodiment, the sub-saturated phase is coupled to a piezoresistive pressure sensor within the microtensiometer via an inorganic nanoporous membrane made of electrochemically-etched porous silicon, the other side of which exists a discrete volume of incompressible liquid such as water. Changes in the degree of sub-saturation result in changes in hydrostatic pressure of the discrete liquid internal to the device that is sensed by the pressure sensor.

The microtensiometer 110 includes a sensor body 112 having an upper layer 130 and an opposing lower layer 132, and a molecularly porous membrane 116 disposed between the upper and lower layers 130, 132. The width of the upper and lower layers 130, 132 and the porous membrane 116 is very large compared to their thickness (e.g., about 100 times larger), and the layers 130, 132 are impermeable to gas (e.g., they are solid). For example, in one embodiment the width (W) of the layers 130, 132 and the porous membrane 116 is 10 millimeters. The thickness ($T_1$) of the upper layer 130 is 300 microns, the thickness ($T_2$) of the lower layer 132 is 500 microns, and the thickness ($T_m$) of the porous membrane 116 is 5 microns (1 micron=1 µm=1×10$^{-6}$ meters). The depth of the circular liquid reservoir cavity 114 is approximately 25 microns.

Sealed within the sensor body 112 is a liquid reservoir 114 that holds a small volume of liquid, such as water. The porous membrane 116 is in fluid contact with the liquid reservoir 114, and extends to an outside edge 134 of the microtensiometer 110. The microtensiometer 110 further includes a sensor 124 adapted to measure changes in the pressure of the liquid reservoir 114. In the illustrated embodiment, a flexible diaphragm 122 is adapted to deflect in response to changes in pressure of the liquid reservoir, and strain gauges 124 sense the deflection. In another embodiment, the measurement of strain could be performed by alternative methods such as an optical measurement of the displacement of the diaphragm (or the depth of the cavity). In one embodiment, the liquid reservoir 114 is the same diameter as the diaphragm 122 (e.g., dimension 2a in FIG. 5).

Figure 6:
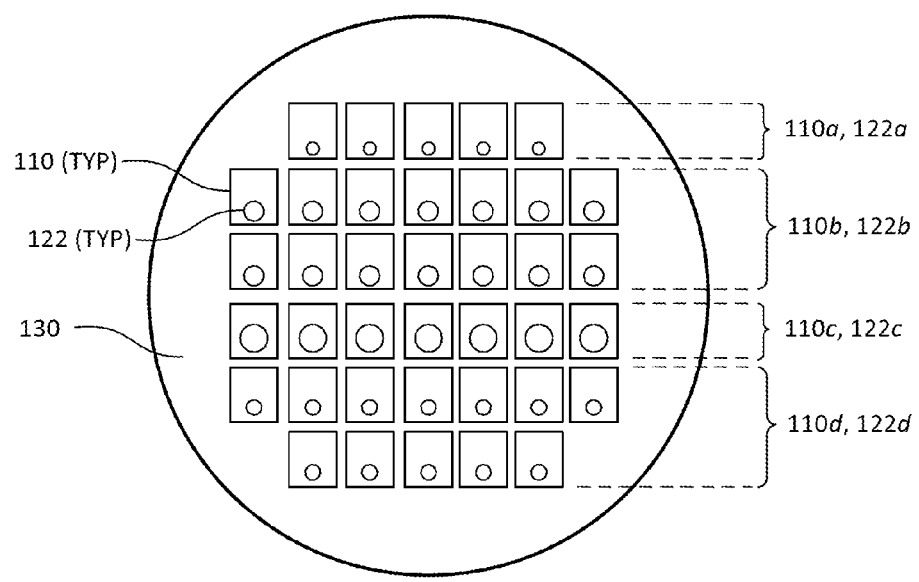
FIG. 6 depicts a top view of an exemplary embodiment of a fabrication approach to manufacture the microtensiometer shown in FIG. 5.

FIG. 6 depicts a top view of an exemplary embodiment of a fabrication approach to manufacture the microtensiometer 110 shown in FIG. 5. The upper layer 130 is formed from a p-type <111> silicon wafer, 100 millimeters (4-inches) in diameter. Thirty eight microtensiometers 110 are organized on the wafer 130, having diaphragms 122 of various diameters. For example, there may be five microtensiometers 110a with a 1.4 millimeter diaphragm 122a; fourteen microtensiometers 110b with a 4 millimeter diaphragm 122b; seven microtensiometers 110c with a 6.8 millimeter diaphragm 122c; and twelve microtensiometers 110d with a 2 millimeter diaphragm 122d.

Figure 7:
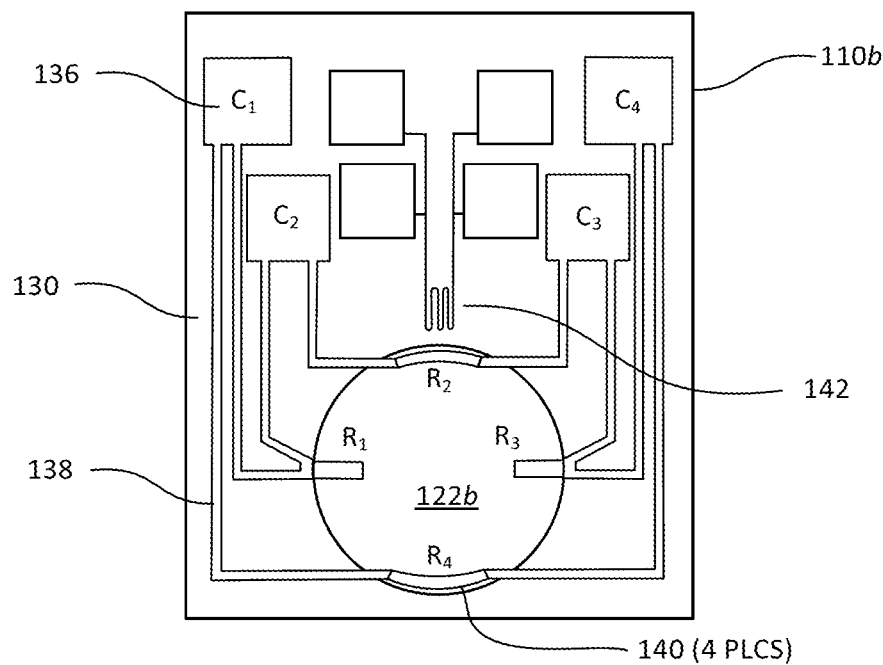
FIG. 7 depicts a top view of the microtensiometer shown in FIG. 5.
Figure 8:
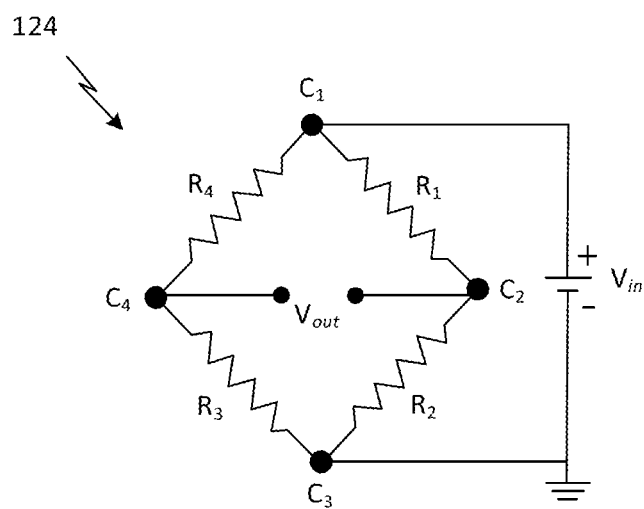
FIG. 8 depicts an exemplary embodiment of a pressure sensor shown in FIG. 7.

FIG. 7 depicts an enlarged top view of the microtensiometer 110b shown in FIG. 6 and, in greater detail, the diaphragm-based pressure transducer 124 that measures the difference between the internal hydrostatic pressure of water in the reservoir 114 and the outside environment (FIG. 5). Contact pads 136 for the Wheatstone bridge are labeled $C_1$-$C_4$, with aluminum leads 138 connected to polysilicon piezoresistors 140, labeled $R_1$-$R_4$. A pressure difference across the diaphragm 122 causes it to deflect (see, for example, FIG. 2), and the resulting strain is measured through piezoresistors 140. In one example, the pressure sensor 124 consists of four doped polysilicon piezoresistors $R_1$-$R_4$ placed atop the circular diaphragm 122 in a Wheatstone bridge configuration. FIG. 8 depicts the Wheatstone bridge 124 configuration of piezoresistors and connections for applied voltage ($V_{in}$) and measured voltage ($V_{out}$). Labels of contact pads and resistors correspond to those in FIG. 7.

For resistances of nearly equal magnitude, the Wheatstone bridge response ($\Delta V_{out}/\Delta V_{in}$) as a function of applied difference in pressure ($\Delta P$), diaphragm dimensions (a-radius [m]; h-thickness [m]), and longitudinal and transverse piezoresistive coefficients, $\pi_l$ and $\pi_t$ [Pa$^{-1}$], can be calculated as:

$$\frac{\Delta V_{out}}{\Delta V_{in}} \approx S\Delta P + \left(\frac{\Delta V_{out}}{\Delta V_{in}}\right)_{OS} \qquad (8)$$

$$S = S = \frac{3a^2}{8h^2}(1-v)(\pi_l - \pi_t) \qquad (9)$$

where S [Pa$^{-1}$] is the sensitivity, v is the Poisson Ratio of polysilicon (~0.23), ($\Delta V_{out}/\Delta V_{in}$)$_{OS}$ is the offset response at $\Delta P=0$; the offset is due to small differences in the resistances of the branches of the Wheatstone bridge and of the contacts to the pads. Calibration of a pressure sensor involves measuring its values of S and ($\Delta V_{out}/\Delta V_{in}$)$_{OS}$.

The microtensiometer 110 may further include a temperature sensor 142. In one embodiment, the temperature sensor 142 is an integrated thin-film platinum resistance thermometer. The integrated platinum resistance thermometer 142 allows for the measurement of temperature which can be used to correct the water potential measurement for differences in (1) temperature from the calibration temperature, and (2) the sample vapor temperature from that of the internal microtensiometer water.

Figure 9:
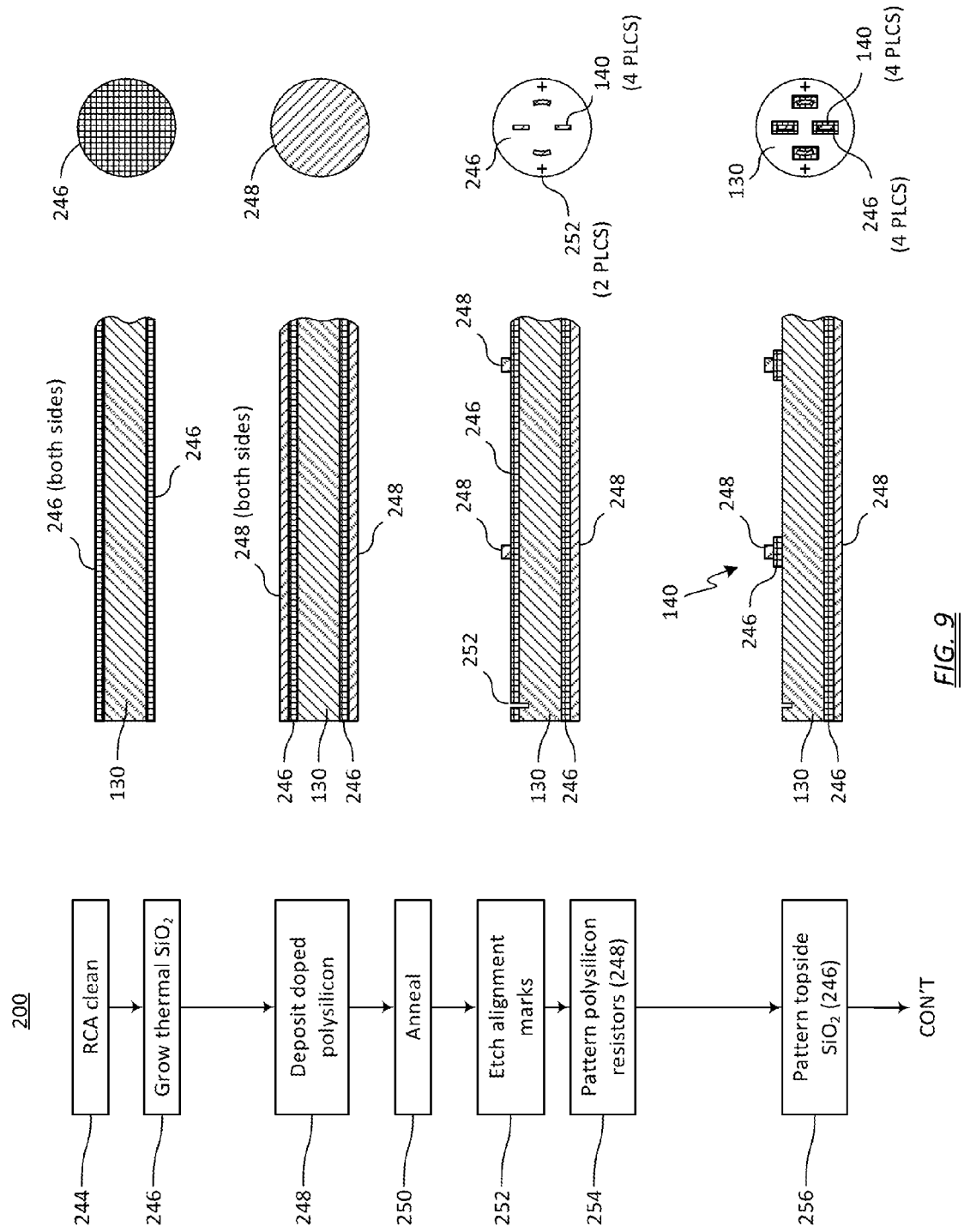
FIG. 9 depicts a flow chart illustrating an exemplary embodiment of a process for fabricating a microtensiometer, and further schematically illustrates the process steps.

FIG. 9 depicts a flow chart illustrating an exemplary embodiment of a process 200 for fabricating a microtensiometer, and further schematically illustrates the process steps. A cross-sectional and top (or bottom) view is illustrated to the right of the process steps. While the numbering of the process steps is presented sequentially, the actual order of operations may be different without departing from the scope of the invention.

In one embodiment of the invention, the upper layer 130 comprises a double-side polished silicon substrate, 100 mm (4 inches) in diameter, 325 µm thick, p-type doping, <111> orientation, and resistivity in the range of 1-10 Ω-cm. The substrates 130 may be procured from University Wafer, http://www.universitywafer.com. The process 200 may include an initial cleaning step 244, such as RCA cleaning, followed by a step 246 to grow a thermal oxide layer (e.g., SiO$_2$) for electrical isolation. In one example, the substrate 130 is baked in a furnace at 1000° C. to achieve a SiO$_2$ thickness of ~1 µm. The process 200 may further include a step 248 to deposit doped p+ polysilicon (e.g., B$_2$H$_6$: SiH$_4$~0.045) over the SiO$_2$ to form the piezoresistors 124. Depositing the doped p+ polysilicon 248 may be carried out using a low pressure chemical vapor deposition (LPCVD) furnace at 620° C. and 400 mTorr to achieve a thickness of ~900 nm. At a step 250, the wafer 130 may be annealed in argon at 900° C. for 30 minutes to enhance the polysilicon strain response and relax residual stresses. Typical resistivities of the LPCVD polysilicon are 18-23 Ω-cm in the pre-annealed condition, and 9-14 Ω-cm in the post-annealed condition.

The process 200 may further include a step 252 to etch alignment marks into the wafer 130 near the outer circumference to align all subsequent mask layers. The process 200 further includes steps 254 and 256 to pattern the polysilicon and topside $SiO_2$ layers using photolithography and dry plasma etching to form the piezoresistors 140 and metal insulation pattern. In one example, the final dimensions of the piezoresistors 140 are 1100 μm×30 μm×1 μm. The photolithographic mask images may be designed using L-m computer-aided design software, available from Tanner EDA, Monrovia, Calif. The mask images may be transferred to a 5-inch by 5-inch fused-silica (quartz) plate ("mask") coated with ~100 nm chromium and photoresist, using a high-resolution pattern generator (Model DWL 2000, available from Heidelberg Instruments, Heidelberg, Germany). Following pattern transfer (e.g., exposure), the photoresist on the exposed mask is developed and the chromium layer wet-etched.

At a step 258, the backside polysilicon layer may be removed by etching, for example, and then at a step 260 the backside $SiO_2$ layer may be removed by etching. Although not illustrated, aluminum may be deposited on the top side at a step 261. Then, at a step 262, the cavity for the liquid reservoir may be patterned and etched to a depth of ~25 μm on the backside of the silicon wafer using deep reactive ion etching (e.g., Bosch process).

At a step 264, a vapor exchange membrane 116 (FIG. 3) comprising nanoporous silicon (PoSi) can be formed on the backside of the silicon wafer 130. The use of wafers with <111> crystallographic orientation may provide more reliable lateral connectivity of pores than the use of <100> orientation. In one example, the setup for the fabrication of PoSi may use a custom-built electrochemical etch cell made of polytetrafluoroethylene (e.g., PTFE or Teflon™). To ensure electrical contact of the silicon wafer to the anode, the wafers may be dipped in 6:1 buffered oxide etch (BOE) solution for 1 minute to remove the native oxide, and then coated with ~200 nm of aluminum by evaporation on the frontside of the wafer (not shown). The backside of the silicon wafer may then be placed in contact with the etchant, which in on example is a 50:50 (v/v) solution of 49% hydrofluoric acid (HF) and 95% ethanol (EtOH) in the etch cell. Electrochemical etching may be carried out under a constant current density of 20 mA/cm² for 5 minutes using a Hewlett Packard DC power supply (Model 6634B). The resulting PoSi layer ($T_m$ in FIG. 5) is approximately 5-6 μm in thickness (depending upon etch time) with a pore size distribution (e.g., pore diameter or $Zr_p$ in FIG. 4) of 1-6 nm. In other example, the pore size distribution may be 1-10 nm. In yet another example, the pore size distribution may be 1-20 nm. The pore size may be determined by porometry, for example. After removing the aluminum on the topside of the wafer at a step 265, the PoSi may be annealed at 700° C. for 30 seconds in an $O_2$ environment at a step 266 in order to replace the hydride-terminated silicon bonds ($SiH_4$) with $O_2$-terminated silicon to form $SiO_2$. This prevents the PoSi from degassing while bonding and filling with water.

At a step 268, the PoSi side of the wafer may be joined to the lower layer 132 to form the body 112 of the microtensiometer (FIG. 5). In one embodiment of the invention, the lower layer 132 is formed of a borosilicate glass wafer (such as Borofloat® or Pyrex'), 100 mm in diameter and 500 μm thick. The porous side of the wafer 130 may be anodically-bonded to the glass wafer 132 in a vacuum at 400° C. and 1200 V DC. In one exemplary method of performing step 268, the glass wafer may be cleaned in a standard SC1 solution (29% $NH_4OH$ and 30% $H_2O_2$ in water at 70° C.) for 10 minutes to remove any organic materials. The silicon wafer 130 may be cleaned by rinsing it with acetone and isopropyl alcohol. The silicon and glass wafers 130, 132 may be dried and plasma cleaned in an oxygen plasma asher (RF 150 W, 4 minutes, 70 sccm $O_2$). Then, the PoSi-side of the silicon wafer 130 may be anodically-bonded to the glass wafer using a substrate bonder, such as Model Sb8e, Süss Microtec, Garching, Germany.

The upper and lower layers 130, 132 are preferably formed of gas-impermeable material. In this manner, the internal liquid reservoir 114 is sealed from the outside environment, exposed only by way of the outside edge 134 of the porous membrane 116.

After bonding, the electrical connections to the piezoresistors 140 may be formed. Following a short (~15 s) 30:1 BOE dip, a thin-film of aluminum (~250 nm) may be evaporated on the front side of the bonded wafer at a step 270. At a step 272, the aluminum may be patterned and wet etched using a solution of phosphoric, acetic, and nitric acids at 50° C. to form the contact pads 136 and leads 138. Aluminum was selected as the thin-film metal as it makes ohmic contact with polysilicon.

At a step 274, electrical isolation and protection of the electronics on the topside of the silicon wafer may be achieved by depositing a stack of PECVD oxide ($SiO_2$; 400 nm), nitride ($Si_3N_4$; 200 nm), and oxynitride ($SiO_2$+15% $Si_3N_4$; 100 nm) at 200° C. This low deposition temperature can be important to prevent debonding of the wafer. Vias may then be opened over the metal pads using photolithography and dry etching. Lastly, individual microtensiometers (e.g., 110a, 110b, 110c, or 110d in FIG. 6) may be released from the wafer by dicing with a wafer saw, such as Model 7100, Kulicke & Soffa. Singapore.

To fill the liquid reservoir 114, individual devices 110 may be placed in a high pressure stainless steel chamber containing deionized water. Water may then be pressurized through the nanoporous exchange membrane 116 at approximately 5 MPa (50 bar) until the internal channels 126 (FIG. 3) and cavity 114 are filled. In one example, microtensiometers 110 may be placed in a vacuum for at least four hours to dry the membrane 116 and evacuate air from the internal cavity. The devices 116 may then be filled by placing them in a HIP pressure chamber filled entirely with deionized water (resistivity 7-18 MΩ) over 12-72 hours. The time to fill the microtensiometers 110 may depend on their internal volumes. For example, the 6.8-mm diaphragm devices may require as much as three days to fill completely at a pressure of 5 MPa. Higher filling pressures should be avoided due to the risk of diaphragm fracture from the high applied strain. For the smaller diaphragm devices (e.g., 1.4 and 2-mm diameter), filling pressures over 10 MPa could be applied and these may be filled within 12 hours.

In use, changes in sub-saturation may be measured using the pressure sensor 124 as the diaphragm 122 deflects in response to changes in internal pressure of water as it equilibrates with the sub-saturated phase through the nanoporous membrane 116.

The water that permeates soils and plants (the soil-plant continuum) presents a particularly important and challenging context for thermodynamic and dynamic measurements. Water in plants and soil controls the terrestrial hydrological cycle via evaporation and transpiration into the atmosphere. On the atmospheric side of these processes, tools for both measurement and prediction have advanced rapidly over the past decades, but they depend on highly simplified models with poorly constrained parameters to describe the status and movement of water in plants and soil. Scientists can predict changes in atmospheric forcing of evapotranspiration, but cannot use such predictions to accurately estimate changes in water status and fluxes in plants and soil. Agriculture depends crucially on the ability to manipulate water within the soil-plant continuum. Current estimates are that agriculture accounts for ~70% of all human water use and that crops exploit only ~40% of the irrigation water deployed.

Tight integration of sensing and irrigation, as part of precision agriculture, promises significant improvements in water use efficiency, but its application has been hindered by the lack of appropriate sensors and insufficient integration and interpretation of their data streams. To respond to unprecedented pressures on our water resources from growing world population and changing climate, better tools need to be developed with which to monitor water in the environment.

A number of fundamental features of the soils and plants make measurements of water status and flux difficult: (1) spatial variations in the properties of the host matrices on both microscopic (e.g., soil-root interface) and macroscopic (e.g., variations through layers of soil) scales; (2) temporal variations due to precipitation and diurnal solar loading; (3) the common presence of water in multiple phases (vapor, liquid, adsorbed on and absorbed within local matrices); (4) strongly non-linear and hysteretic constitutive equations that relate chemical potential and permeability to water content; (5) strong coupling to temperature and its gradients; and (6) the importance of states that are below but near saturation with respect to water. These characteristics define strict criteria on the properties (dimensions, response times, accuracy, and range) and modes of use (simultaneous measurements of content, chemical potential, and temperature) of water sensors for the soil-plant continuum. They also demand close integration with appropriate mathematical models of both physical and biological phenomena.

Embodiments of the present invention integrate microengineering and physical chemistry of water, soil science and hydrology, and plant physiology and horticulture to develop a complete sensing framework for water status and flux in soils and plants. Disclosed herein is a miniature, multimodal sensor of water chemical potential, water content, and temperature, the three critical variable that define the state of water in soils and plants. The multimodal sensor may also be referred to throughout this disclosure as a $\Psi\Theta T$-sensor.

Water relations refer to the thermodynamics and dynamics of water and the associated thermal transport processes. At the continuum scale (e.g., large compared to the typical pore and cell dimension), three state variables are required to characterize these relations fully. The first state variable is the chemical potential or water potential defined as, $\Psi=(\mu-\mu_0)/\overline{v}_l$ [Pa], where $v$[J/mole] is the chemical potential of water in the phase of interest, $\mu_0$ is for pure water at standard pressure ($P_0$=0.1 MPa) and temperature (25° C.) (STP), and $\overline{v}_l$[m$^3$/mole] is the molar volume of liquid water at STP. Physically, the water potential of a phase is the pressure relative to atmospheric in pure liquid in equilibrium with that phase. The water potential provides the most generally useful measure of the accessibility of water for chemical processes or physical exchange between phases or matrices. It includes all contributions to the energetic state of water: gravity, pressure, osmotic pressure, relative humidity, and interactions with solid matrices. The second state variable is water content or volume fraction, $\Theta=+V_w/V_w+V_m)$ [M$^3$/m$^3$], where $V_w$ and $V_m$ are the volumes of water and of matrix. Tracking $\Theta$ in space and time is necessary to evaluate fluxes of water and thermal energy and to provide information on the structure and composition of the soil or tissue (e.g., with respect to liquid and vapor fractions). The third state variable is temperature, T [K]. Temperature influences material properties, phase equilibria, and transport rates, and gradients of temperature drive fluxes of both energy and water.

Among these variables, $\Psi$ is the most valuable and the most challenging to measure. Its usefulness stems from its generality as a quantification of water status. For example, at the same water content, two different soil types can have radically different water potentials: at $\Theta$=0.2 in clay, $\Psi_c$~−0.01 MPa and in sandy loam, $\Psi_{s1}$~−1 MPa. For the extraction of water by a plant via transpiration or by direct surface evaporation, it is the values of $\Psi$ that matters. Thus, for the same water content, water in sandy loam is 100-fold more accessible (thermodynamically) than in clay. Within a plant, $\Psi$ determines viability, growth potential, yield, and quality of crop. The intrinsic challenges of measuring $\Psi$ stem from its range of values in plants and soils ($-10^{-3}>\Psi>-10$ MPa): 1) the values are negative, representing sub-saturation. For example, the water potential of a unsaturated vapor at STP, $\Psi=(RT/\overline{v}_1)\ln(RH/100)$, where R is the ideal gas constant and RH is the relative humidity; for RH<100, $\Psi$<0. In most cases, these negative values cannot be measured directly as mechanical pressures as is possible for bulk liquids flowing in pipes and streams. 2) The range extends over four orders of magnitude, challenging the resolution and accuracy of any single measurement technique. 3) While broad, this range lies very close to saturation, corresponding in the vapor phase to 99.99>RH>93.0.

The coupling of $\Psi$, $\Theta$, and T are crucial for understanding water relations and present important challenges for the design and operation of water sensors. Experimental and theoretical treatments of water relations are often performed with an assumption of isothermal conditions, despite recognition of the strong coupling of temperature to the thermodynamics and transport of water, the daily occurrence of strong temperature gradients (>>10° C./m) within the soil and plants, and the importance of water in plants and soils in defining the energy budget of the earth's surface. The coupling is apparent in the complete equations for water and thermal energy shown in Table 1 in a condensed form: gradients of temperature drive mass flow and gradients of water potential drive heat flow (Equation 10). The cross-coupling ($K_{wq}$ and $K_{qw}$) is particularly strong in unsaturated porous media (typical of both soil and plant tissue) due to the large thermal expansivity of the gas phase, temperature dependence of surface tension, and transport of latent heat with evaporation and condensation. Numerical analysis of Equations 10 and 11 indicate that neglect of $\Psi$-T coupling can lead to large errors (10-50%) in predictions of flux and of spatial and temporal variations in $\Psi$ and T in both soils and plant tissues. In the context of sensing $\Psi$, the neglect of temperature effects can lead to significant errors.

TABLE 1

Non-isothermal water relations

Flux:     $J_w = -\rho_w (K_{ww} \nabla \Psi + K_{wp} \nabla T)$    $J_q = -\rho_w K_{qw} \nabla \Psi - \lambda \nabla T$     (10)

Conservation:     $\rho_w \dfrac{\partial \theta}{\partial t} = \nabla \cdot J_w - S_p$    $C_{tot} \dfrac{\partial T}{\partial t} = \nabla \cdot J_q - c_l J_w \cdot \nabla T$     (11)

In the condensed equations shown in Table 1, the fluxes $J_w$ and $J_q$, the permeabilities $K_{ww}$, $K_{qw}$ and $K_{wq}$, and the thermal capacitance $C_{tot}$ contain contributions from both the vapor and liquid phases. $\rho_w$, [kg/m$^3$] is the effective mass density of water in both vapor and condensed phases (~liquid density, $\rho_l$); $S_p$ [kg/m$^3$/s] is the volumetric sink representing water uptake by roots in soil; $C_{tot}$ [J/K/m$^3$] is total heat capacity due to all phases; $J_w$ [kg/m$^2$/s] is the flux of water in both the liquid and vapor phases, $J_q$ [W/m$^2$] is the heat flux due to conduction, convection (ignoring vapor sensible heat), and phase change; $c_l$ [J/kg] is the heat capacity of liquid water; $K_{ww}$ [m/s/Pa] is the generalized Darcy permeability that accounts for transport in both the liquid and vapor phases; $K_{wq}$ [m$^2$/K/s] is the thermodiffusion coefficient; $K_{qw}$ [m$^5$/kg/s] captures thermal transport with phase change and thermally induced mass flows; and $\lambda$ [W/m/K] is the global thermal conductivity due to all phases.

Further coupling of $\Psi$, $\Theta$, and T enters through the constitutive relations that are required to solve Eqs. 10 and 11: the $\Psi$- and T-dependence of $\Theta$, $K_{ww}$, $K_{wq}$, $K_{qw}$, $\lambda$, $S_p$ and $C_{tot}$. The measurement of the water retention curve, $\Theta(\Psi, T)$ and the permeability, $K_{ww}(\Psi,T)$ as a function of soil type and plant species represents a ubiquitous, fundamental and challenging component of hydrology, plant physiology, and related applied fields. These functions are strongly non-linear (e.g., $\Theta \sim \ln(-\Psi)$ in most soils), hysteretic, and, in the context of plants, coupled to complex biological responses. The other relations are less well characterized due to the lack of appropriate tools in the lab and field: the forms for the conductivities, $K_{wq}$, $K_{qw}$, and $\lambda$, and the capacitance, $C_{tot}$ have reasonably strong theoretical basis, but have been rarely measured; forms for the water uptake by plants, $S_p$ have a weak theoretical basis informed by only a few direct experiments.

Thus, important deficiencies exist in the understanding of water relations in soils and plants and in the ability to characterize them experimentally and exploit them in the field. The integrated sensing framework for $\Psi$, $\Theta$, and T disclosed herein may provide a revolutionary new tool set with which to tackle both fundamental and practical challenges in this domain.

Figure 10:
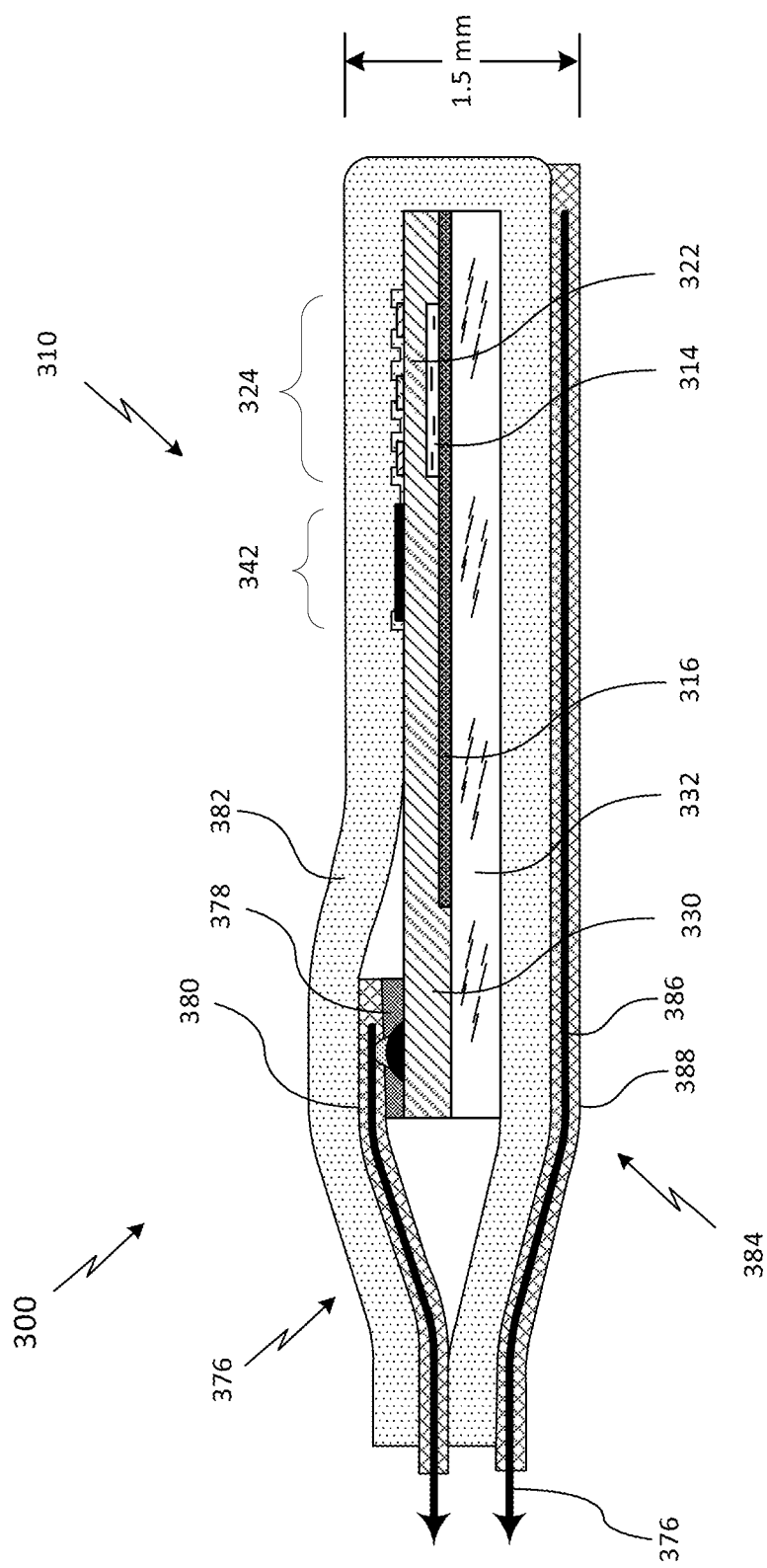
FIG. 10 depicts a cross sectional view of a multimodal sensor according to one embodiment of the present invention.
Figure 11:
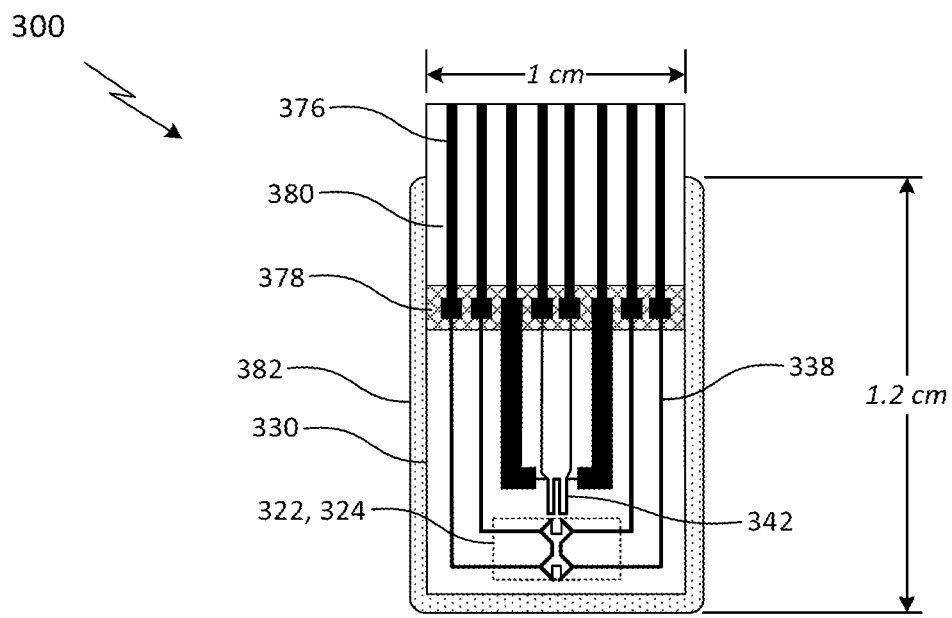
FIG. 11 depicts is a top view of the multimodal sensor shown in FIG. 10.

Turning now to FIGS. 10 and 11, wherein like numerals indicate like elements from FIGS. 1-9, shown is an integrated multimodal sensor 300 for measuring water potential $\Psi$, water content $\Theta$, and temperature T according to one embodiment of the present invention. FIG. 10 depicts a cross-sectional illustration of sensor 300, and FIG. 11 depicts a top view. The multimodal sensor 300 includes a microtensiometer as disclosed hereinabove adapted to measure water potential $\Psi$. That is, the microtensiometer includes an upper layer 330 formed of silicon substrate, a Tower layer 332 formed of borosilicate glass, a sealed internal liquid reservoir 314, and a porous membrane 316 disposed between the upper layer 330 and lower layer 332. The porous membrane 316 is in fluid contact with the liquid reservoir 314 and extends to an outside edge of the microtensiometer. The microtensiometer 310 further includes a diaphragm-based pressure transducer 324 that measures the internal hydrostatic pressure of water in the reservoir 314. A pressure difference across the diaphragm 322 causes it to deflect, and the resulting strain is measured through four doped polysilicon piezoresistors placed atop the circular diaphragm in a Wheatstone bridge configuration.

The multimodal sensor 300 further includes a thin film platinum resistance thermometer 342 to provide temperature data. For the range of temperatures relevant in soils and plants (~0-40° C.), platinum resistance thermometers (PRTs) with four-point probe measurement are generally considered to be most accurate ($\Delta T$~0.01 K) when calibrated. PRTs can also be formed in a single lithographic step. In one embodiment, chip-on-film electrical connections 376 may connect the leads 338 to the Wheatstone bridge 324 and platinum resistance thermometer 342 using on anisotropic conductive adhesive (ACA) 378 for electrical bonding and lithographically patterned copper-on-poly(imide) film 380 for wiring. This strategy adds minimally to the thickness and improves stability of bridge measurements with respect to both mechanics and drift. Further, the conductive contact through the ACA film is automatically insulated by the surrounding, nonconductive epoxy.

In another embodiment, conventional wire bonding to printed circuit board and potting in a water-resistant epoxy may be utilized. However, this alternative will increase the thickness by ~0.5 mm.

The multimodal sensor 300 may further include a semi-permeable sheath 382 or vent comprising a hydrophobic highly crystalline polytetrafluoroethylene polymer which has a microstructure characterized by nodes interconnected by fibrils. In one example, the polytetrafluoroethylene polymer is a GORE-TEX® membrane available from W. L. Gore & Associates, inc. The GORE-TEX® sheath 382 may be formed and secured to the surface of the microtensiometer sensor by a silicon adhesive backing, for example, providing a tight, sealed envelope around the sensor 300.

In one embodiment, the pores in the sheath 382 are approximately 0.02 micrometers to 10 micrometers in size, which is about 20,000 times smaller than a water droplet, but 700 times larger than a water vapor molecule. The hydrophobic membrane will provide a vapor space of well-defined thickness between the edge of the membrane and the outside environment. This gap allows for equilibration of water while preventing equilibration of free solutes that may exist in the external environment to enter the device. One advantage to this embodiment is that the hydrophobic, microporous structure will resist the entry of aqueous solutions up to pressure differences of 0.6 bar (0.06 MPa) while allowing for vapor exchange. In some embodiments, the sheath 382 includes a protective layer of nylon fabric (not shown). In other embodiments, the sheath 382 may be formed of hydrophobized, porous ceramics or reverse osmotic membrane with low molecular weight cut-off.

The multimodal sensor 300 may further include an integrated water content sensor 384. In one embodiment, a thin-film wave guide may be formed between laminated layers of poly(imide) for time-domain reflectometry (TDR). Time-domain reflectometry excites a pair or an array of parallel electrodes ("waveguides") with an AC electrical pulse in the GHz range and measures the time delay for the reflection of this pulse. With the electrodes embedded in the medium of interest, the time delay, $\Delta t \sim 2\sqrt{\in_r}/c$, where L [m] is the length of the electrodes, $\in_r$ is the relative dielectric permittivity of the medium, and c [m/s] is the speed of light. Given the large dielectric permittivity of water ($\in_r=80$) relative to that of the solid components of soils and plant tissue ($\in_r \sim 4$), $\Delta t$ varies significantly with water content, allowing for an accuracy, $\Delta \Theta \sim 2\%$ across the full range of $\Theta$ in the soil or tissue.

Figure 12:
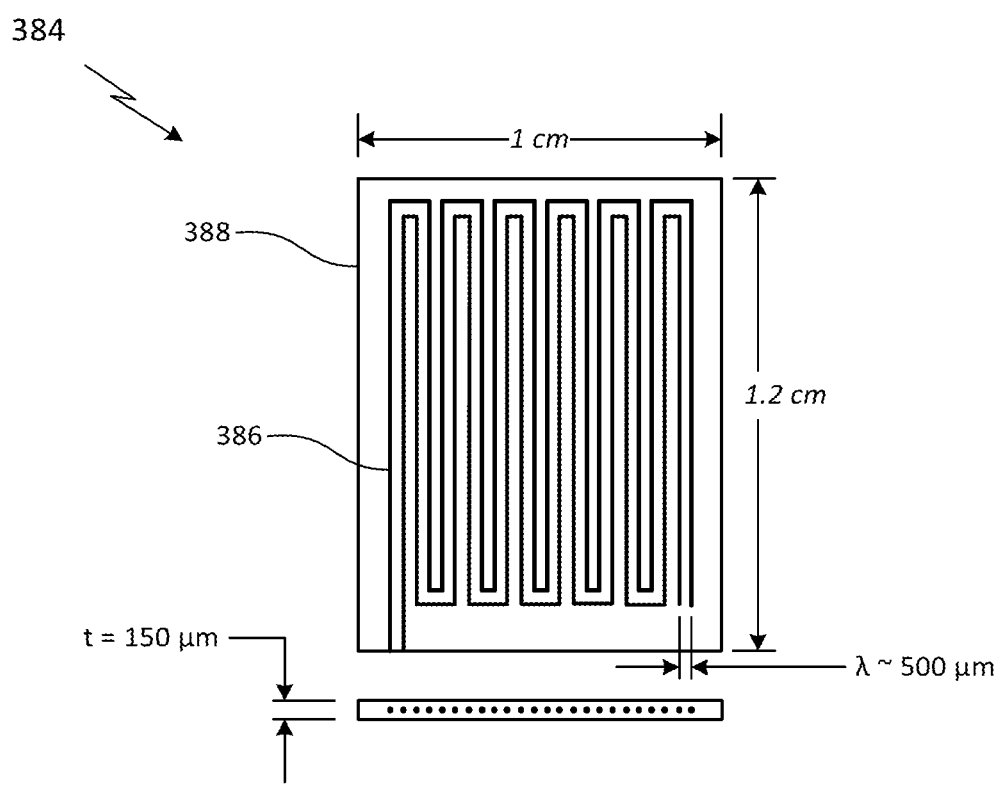
FIG. 12 depicts a top view of a thin-film wave guide according to one embodiment of the invention.

As shown in FIG. 10, a custom waveguide 384 may be integrated with the microtensiometer 310 and platinum resistance temperature sensor 342 and with existing TDR acquisition equipment, such as Campbell Sci. TDR100. Turning to FIG. 12, in one embodiment of the invention the waveguide 384 may be formed by lithographically patterning copper 386 on a flexible laminate 388. In one example, the waveguide may be formed with DuPont's Pyralux TK copper-clad films and bonding layers. The film system, which contains fluoropolymer, will encapsulate the waveguides between thin layers with low dielectric constant ($\in_r \sim 2.3$), low water adsorption (0.6% by mass), and good environmental stability. The package will separate the waveguide 384 from the external medium with ~50 μm of film. In one example, the electrode separation $\Delta$ is ~500 μm, and the pair of electrodes are designed to have a total length L>10 cm for an expected accuracy $\Delta \Theta \pm 0.02$ m$^3$/m$^3$. The flexible TDR waveguide 384 may be adhered to the backside of the assembly as illustrated in FIG. 10.

Figure 13:
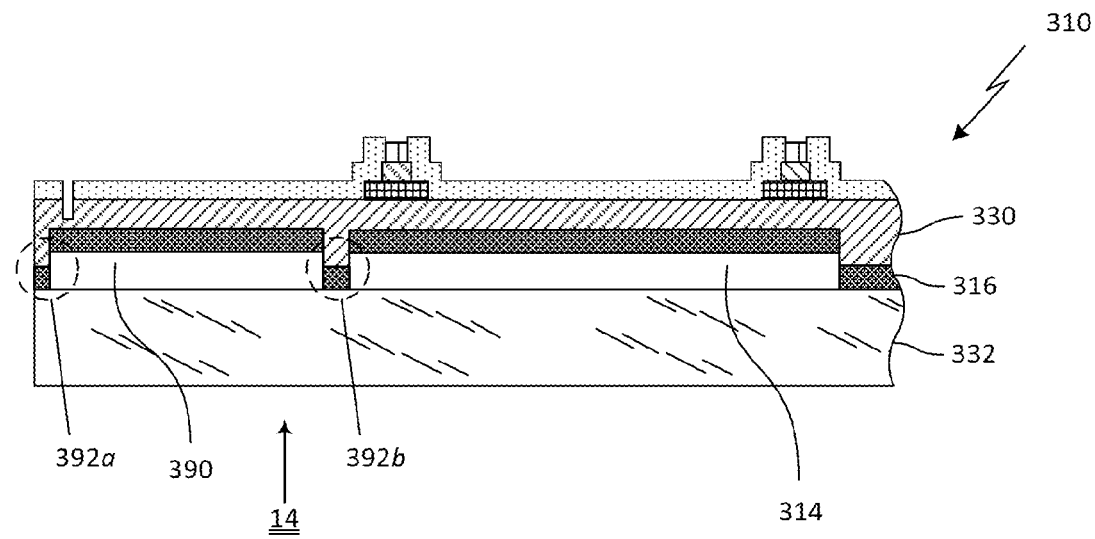
FIG. 13 depicts a cross sectional view of a microtensiometer with permeability channels.
Figure 14:
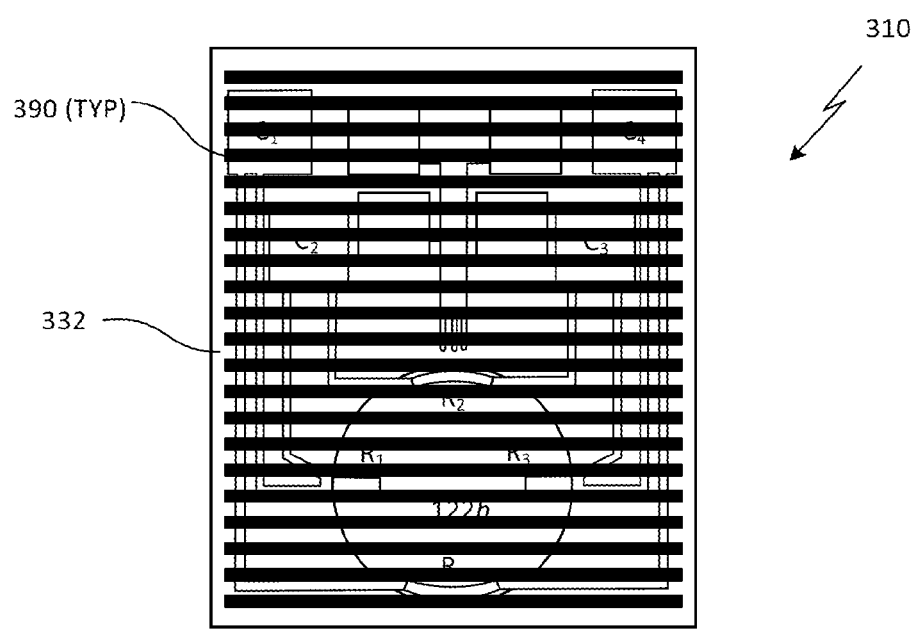
FIG. 14 depicts a bottom view of the microtensiometer shown in FIG. 13.

FIG. 13 depicts a cross sectional view of the microtensiometer 310 shown in FIG. 9, and FIG. 14 depicts a bottom view of the sensor 310 looking through the borosilicate glass 332. The multimodal sensor 300 may further include an array of channels 390 patterned into the upper layer 330 and/or lower layer 332 to increase the permeability of the membrane 316 without changing the global dimensions of the sensor. That is, the channels 390 partially 10 bridge the distance from the reservoir to the edge of the sensor to reduce the distance water travels through the porous silicon without adding significant internal volume. In one example, depicted in MG. 13, the array of channels 390 are etched in the bottom side of the silicon wafer 330 to the same depth (and in the same step) as the reservoir 314 for the liquid. These channels 390 are closed at either end; they do not reach either the edge of the sensor or the liquid reservoir 314. The regions 392a of membrane 316 that separate the channels 390 from the edge ensure that air does not penetrate the channels. The regions 392b of membrane 316 that separate the channels from the reservoir ensure that any air of vapor that emerges in a channel due to cavitation (boiling) does not enter the reservoir and disrupt operation of the device.

In another aspect of the invention, a procedure is described to calibrate the TDR waveguide 384 and further described is a new technique for measuring water retention curves ex situ. While reasonable correlations exist for the dielectric response of a number of soil types, none exist for plant tissue and better accuracy is achieved when TDR probes are calibrated with the material of interest. FIG. 15 depicts a system that can be used to gravimetrically calibrate the thin-film waveguides 384 integrated in the disclosed multimodal sensor as a function of temperature and water content. A multimodal sensor 300 can be fixed on the floor of a thermostated container 1100 beneath a thin layer of the sample of interest (S) (e.g., soil or explained tissue). The entire system will sit on a balance 1102 (1 kg capacity, ±1 mg). A rigid metal mesh may compress the sample slightly. The sample (S) may be fully wetted initially and allowed to dry into the ambient air. For most materials of interest, the heat and mass transfer from a thin sample (≤1 cm) should be strongly limited by the natural convection in the air, such that gradients in the sample will be weak. In a period of a few days, the thin samples will lose almost all water in a typical dry laboratory environment. For dry mass, the sample will be oven dried (105° C. for 24 hours) and weighed again. With continuous measurements of mass and TDR time delay, a calibration curve, $\Delta t(\Theta,T)$ can be constructed. Importantly, with the continuous measurements of mass and water potential, an isothermal water retention curve for the sample, $\Theta(\Psi,T)$ may be constructed across an unprecedented range. This experiment, enabled by the multimodal sensor 300, has the potential to become a new standard for measuring water retention ex situ (and sorption analysis more generally), as no existing technique provides equivalent range or simplicity. The impact that potential deformation or cracking of the sample might have on $\Delta t(\Theta,T)$ and $\Theta(\Psi,T)$ can be characterized, and compared to the $\Theta(\Psi)$ measured on a pressure plate extractor (soil) and point measurements from a chilled mirror hygrometer (plant tissue). With cycles of rewetting, this system can be used to characterize the secondary wetting curves (hysteresis).

In another aspect of the invention, appropriate packaging for the multimodal sensors and methods of insertion into soil may be developed working with packed soil columns. The water relations of a soil, especially in the wet regime, are known to be sensitive to mechanical disruption. In one packaging example, the sensor may be clamped in a frame formed of stainless steel rods such that both the TDR waveguide and the tensiometer membrane are exposed to the surrounding medium. The rigid frame may have a tapered tip. In calibrated soils representing a range of hydraulic and mechanical properties (e.g., sand, sandy loam, silt loam), multiple probes may be inserted to the same depth (e.g., 4 cm) using different strategies (e.g., from most to least disruptive). For example, 1) placement in a large bore with repacking around the probe, 2) insertion into a narrow slit opened with a flat rod of dimension similar to that of probe, and 3) direct insertion of probe with no guide hole. The vertical insertion may first be characterized, as this orientation is favored with conventional TDR to avoid artifacts due to hindered transport along the vertical axis by the probe. The least disruptive technique may then be selected that can be performed reliably without damaging the probe.

Despite having been proposed over sixty years ago, the governing principles of water relations in soils remain unchallenged by complete experiments, in particular under non-isothermal conditions. The disclosed multimodal sensor may be exploited to provide a rigorous experimental examination of water relations in soils and lay the foundation for its use in the field. The Wind evaporation method that provides access to near-isothermal water relations in the highly saturated limit (and is traditionally run with conventional tensiometers, no thermal loading, and no forced convection over the soil) may be expanded upon. The experiments may allow the methods to mature in a context that is directly translatable to the field. Moreover, the experiments may provide the first experimental characterizations of water relations deep into the unsaturated, non-isothermal regime that dominates in surface layers of exposed soils in arid climates and under draught conditions. For example, experiments may be conducted in three soils that span a range of permeabilities and water retention properties (e.g., sand, sandy loam, silt loam). Water retention curves may be established and the TDR may be calibrated with those soils prior to these experiments. FIGS. 16 and 17 show the experimental system with multimodal sensors $S_1$-$S_4$ deployed at four depths in an insulated column 1104 that is thermally regulated ($T_0$) and fed at its base. Soil samples 1106 can be characterized in the lab with respect to both equilibrium (e.g., water retention curves) and non-equilibrium (e.g., hydraulic permeability and thermal conductivity) properties. These probes and this application can also benefit from the inclusion of the thin film TDR. Evaporation occurs with or without radiative forcing and forced convection. Surface temperature, $T_{surf}$ is measured remotely with an IR thermometer 1108; base temperature, $T_0$ is controlled by a controller 1110. Forced convection in the air above the column can be used with a heat lamp to tune the evaporative potential and generate large thermal gradients (i.e., $T_{surf}$-$T_0$=10° C.). The process can be run to water potentials of at least –10 MPa or until steady state conditions are achieved. Measurements of $\Psi$ can be tested against chilled mirror dew point with samples extracted at the end of the experiment. This system can be exploited to extract time-dependent profiles of $\Psi$, $\Theta$, T and fluxes of heat and mass. With these data that cover an unprecedented range of conditions, the parameterizations of the 2DHydrus numerical package can mature and adapt its protocols for parameter estimation. Alternative fitting procedures can be used (e.g., based on splines) to handle strong non-linearity in the unsaturated regime, if necessary. Using fits from sub-sets of the data, the minimal number of probes necessary to generate accurate water relations can be identified. In a second stage, the time-dependent forcing (diurnal thermal loading and precipitation) can be simulated and the multi-dimensional gradients that will be encountered in field conditions.

Figure 18:
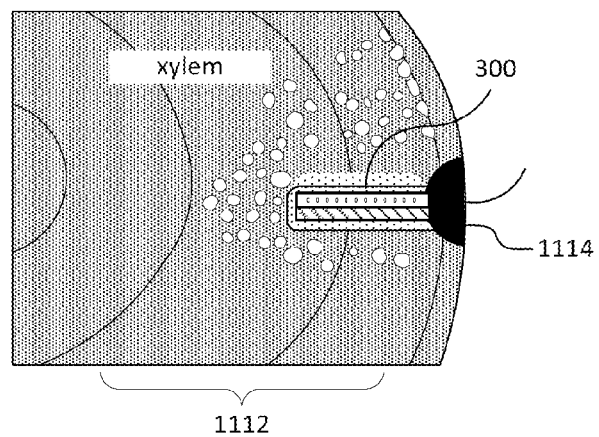
FIG. 18 depicts a cross sectional view of a multimodal sensor embedded within the xylem tissue of the stem of a plant.
Figure 19:
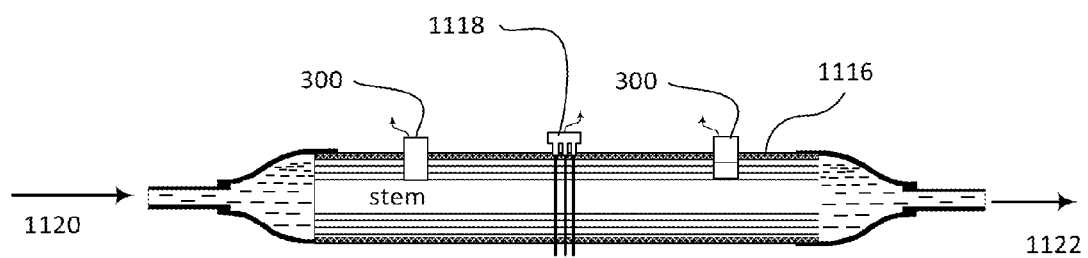
FIG. 19 depicts a cross sectional view of a sensor system to measure the conductance of the xylem tissue in an excised stem of a plant.

FIGS. 18 and 19 illustrate a method to embed the microtensiometer with integrated PRT within the xylem tissue 1112 of the stem of a plant for complete plant water relations, in situ. In one example, embedding strategies can be developed in cut branches of woody plants with typical diameter of 2-3 cm. As illustrated in FIG. 18, the multimodal sensors 300 can be embedded with the thin axis orthogonal to the axis of the xylem vessels. This orientation will minimize the obstruction of vessels by the probe. Further, preliminary studies embedding dummy probes (plastic pieces with the dimensions of the microtensiometer) in grape vines in the field indicated that this orientation led to less scarring (~100 μm-thick scar) than other orientations. A guide slit can be cut with a razor blade and opened gently with a chisel blade to accommodate the multimodal sensor snuggly, with the body of the sensor completely beneath the level of the bark. The opening around the wires can be sealed with pruning sealing putty 1114.

Despite extensive research, significant uncertainty remains relating to the conductive properties of xylem tissue. For example, this uncertainty relates to the prevalence of and response to cavitation events in the presence of water stress, the importance of water content versus water potential in defining conductance, and the change in xylem conductance with changing composition of the sap. Recent work raises important doubts about the interpretation of the most commonly used, ex situ experimental methods. This uncertainty also compromises work in soil hydrology by propagating into the water uptake of roots.

The multimodal sensor disclosed herein will allow development of methods to address these questions with simultaneous, multi-point measurements, in situ. The laboratory experiments described herein may lay a foundation of field-ready methods by making use of portable logging instrumentation.

FIG. 19 illustrates a method to measure the conductance of the xylem tissue in an excised stem of a plant. Shown is an axial cross-section of stem segment 1116 with two multimodal sensors 300 embedded at different axial positions and one embedded sap-flow meter 1118 between them. In one example, the stem segment is a cut branch of poplar having a range of water potential equal to 0 to –3 MPa. A water retention curve may be established and the the TDR calibrated with poplar tissue prior to the experiments. Commercial sap flow sensors provide moderate resolution of sap flux (~±2 g/m²/s or ±10%) based on measuring convective transfer of a heat pulse. A pressure-driven flow of aqueous solution 1120 with fixed water potential ($\Psi_s$) and temperature ($T_s$) (tuned with osmotic content) or gas at controlled relative humidity can be driven through the branch. The total liquid flow can be collected and measured on a balance 1122. With this system, the response of both the tensiometer and the TDR with respect to the resolution (in time and magnitude) of water potential in the xylem vessels and water content in the surrounding tissue can be characterized. The impact of temperature gradients between the sap and the tissue can also be characterized; such gradients are expected on hot days as cool water from the soil moves up the plant. In combination with the sap flow readings, optimal procedures for extracting conductivities ($\Delta\Psi_{12}/J_w$, where $\Delta\Psi_{12}$ is read between the two sensors) can be established. This unprecedented capability to reexamine questions of the dependence of conductance on the ionic composition of sap and on degree of embolization (gas filled vessels due to cavitation) can be exploited.

While the present invention has been described with reference to a number of specific embodiments, it will be understood that the true spirit and scope of the invention should be determined only with respect to claims that can be supported by the present specification. Further, while in numerous cases herein wherein systems and apparatuses and methods are described as having a certain number of elements it will be understood that such systems, apparatuses and methods can be practiced with fewer than the mentioned certain number of elements. Also, while a number of particular embodiments have been described, it will be understood that features and aspects that have been described with reference to each particular embodiment can be used with each remaining particularly described embodiment.

What is claimed is:

1. A microtensiometer, comprising:
   a sensor body comprising a first gas-impermeable layer and an opposing second gas-impermeable layer, the sensor body defining an internal liquid reservoir;
   a porous membrane layer disposed between and in contact with the first gas-impermeable layer and the opposing second gas-impermeable layer and in fluid contact with the internal liquid reservoir, the porous membrane layer extending to an outside edge of the microtensiometer, the porous membrane layer defining a plurality of through pores, the pores providing an open path from the internal liquid reservoir to the outside edge of the microtensiometer, the pores having a maximum diameter of 3 millimeters; and a sensor adapted to measure changes in pressure between the internal liquid reservoir and an outside environment.

2. The microtensiometer according to claim 1, wherein the first gas-impermeable layer is formed of silicon substrate.

3. The microtensiometer according to claim 1, wherein the opposing second gas-impermeable layer is formed of borosilicate glass.

4. The microtensiometer according to claim 1, wherein the internal liquid reservoir is formed in first layer.

5. The microtensiometer according to claim 1, wherein the porous membrane layer is formed of porous silicon.

6. The microtensiometer according to claim 1, wherein the porous membrane layer is anodically-bonded to the opposing second gas-impermeable layer.

7. The microtensiometer according to claim 1, wherein the pores have a pore size distribution of 1-20 nm.

8. The microtensiometer according to claim 7, wherein the pores have a pore size distribution of 1-6 nm.

9. The microtensiometer according to claim 1, wherein the pores have a maximum diameter of 0.3 millimeters.

10. The microtensiometer according to claim 1, further comprising a flexible diaphragm adapted to deflect in response to changes in pressure of the internal liquid reservoir, the sensor being coupled to the flexible diaphragm and adapted to measure a strain resulting from a deflection.

11. The microtensiometer according to claim 10, wherein the sensor comprises polysilicon piezoresistors arranged in a Wheatstone bridge.

12. The microtensiometer according to claim 10, wherein the flexible diaphragm is integral with the first gas-impermeable layer.

13. The microtensiometer according to claim 1, further comprising an integrated thin-film platinum resistance thermometer.

14. The microtensiometer according to claim 1, further comprising a plurality of internal channels adjacent the porous membrane layer, the internal channels extending between but exclusive of the sealed internal liquid reservoir and the outside edge of the microtensiometer.

15. The microtensiometer according to claim 14, wherein the internal channels are formed in the first gas-impermeable layer.

16. A multimodal sensor, comprising:
a microtensiometer adapted to measure chemical potential of a sub-saturated liquid, the microtensiometer comprising a sensor body, the sensor body comprising a first gas-impermeable layer and an opposing second gas-impermeable layer, the sensor body defining an internal liquid reservoir; a porous membrane layer disposed between and in contact with the first gas-impermeable layer and the opposing second gas-impermeable layer and in fluid contact with the internal liquid reservoir, the porous membrane layer extending to an outside edge of the microtensiometer, the porous membrane layer defining a plurality of through pores, the pores providing an open path from the internal liquid reservoir to the outside edge of the microtensiometer, the pores having a maximum diameter of 3 millimeters; and a sensor adapted to measure changes in pressure of the internal liquid reservoir;
a temperature sensor integrated onto the sensor body; and
a water content sensor coupled to the sensor body.

17. The multimodal sensor according to claim 16, further comprising a semipermeable sheath adapted to provide a defined vapor space between the outside edge of the porous membrane layer and an outside environment.

18. The multimodal sensor according to claim 17, wherein the semi-permeable sheath comprises pores sized approximately 0.02 micrometers to 10 micrometers in size.

19. The multimodal sensor according to claim 16, further comprising a chip-on-film electrical connection to a sensor lead wire.

20. The multimodal sensor according to claim 19, wherein the chip-on-film electrical connection comprises lithographically patterned copper-on-poly (imide) film bonded to the sensor lead wire by anisotropic conductive adhesive.

21. The multimodal sensor according to claim 16, wherein the water content sensor comprises a thin-film wave guide for time-domain reflectometry.

22. The multimodal sensor according to claim 21, wherein the thin-film wave guide comprises lithographically patterned copper on a flexible laminate.

23. The multimodal sensor according to claim 16, wherein the microtensiometer further comprises a plurality of internal channels adjacent the porous membrane layer, the internal channels extending between but exclusive of the internal liquid reservoir and the outside edge of the microtensiometer.

* * * * *

UNITED STATES PATENT AND TRADEMARK OFFICE
CERTIFICATE OF CORRECTION

PATENT NO. : 9,766,173 B2  Page 1 of 1
APPLICATION NO. : 14/898003
DATED : September 19, 2017
INVENTOR(S) : Abraham D. Stroock et al.

It is certified that error appears in the above-identified patent and that said Letters Patent is hereby corrected as shown below:

In the Specification

At Column 1, Line 16, insert:
--STATEMENT REGARDING FEDERALLY FUNDED RESEARCH OR DEVELOPMENT
This invention was made with government support under 0747993 awarded by the National Science Foundation, FA9550-09-1-0188 awarded by the Air Force Office of Scientific Research and 2012-67021-19298 awarded by the United States Department of Agriculture. The Government has certain rights in the invention.--

Signed and Sealed this
Twenty-eighth Day of November, 2017

Joseph Matal
*Performing the Functions and Duties of the
Under Secretary of Commerce for Intellectual Property and
Director of the United States Patent and Trademark Office*